(12) United States Patent
Keeton et al.

(10) Patent No.: US 10,571,433 B2
(45) Date of Patent: Feb. 25, 2020

(54) ADJUSTABLE FIXTURE FOR SCANNING ACOUSTIC MICROSCOPY

(71) Applicant: Sonix, Inc., Springfield, VA (US)

(72) Inventors: Paul Ivan John Keeton, Woodbridge, VA (US); James Christopher Patrick McKeon, Woodbridge, VA (US); Michael Lemley Wright, Fredicksburg, VA (US); Kevin John Brault, Chandler, AZ (US)

(73) Assignee: Sonix, Inc., Springfield, VA (US)

( * ) Notice: Subject to any disclaimer, the term of this patent is extended or adjusted under 35 U.S.C. 154(b) by 221 days.

(21) Appl. No.: 15/651,221

(22) Filed: Jul. 17, 2017

(65) Prior Publication Data

US 2018/0128782 A1 May 10, 2018

Related U.S. Application Data

(60) Provisional application No. 62/417,482, filed on Nov. 4, 2016.

(51) Int. Cl.
*G01N 29/06* (2006.01)
*G01N 29/22* (2006.01)

(52) U.S. Cl.
CPC ....... *G01N 29/0681* (2013.01); *G01N 29/223* (2013.01)

(58) Field of Classification Search
CPC ............ G01N 29/0681; G01N 29/223; G01N 2291/2697; H01L 21/6732; H01L 21/68714; H01L 21/68721
USPC .................................................. 73/663–669
See application file for complete search history.

(56) References Cited

U.S. PATENT DOCUMENTS

| | | | | |
|---|---|---|---|---|
| 5,440,920 | A * | 8/1995 | Jung | G01Q 20/02 73/105 |
| 5,631,425 | A * | 5/1997 | Wang | G01N 29/0681 73/597 |
| 2001/0001894 | A1* | 5/2001 | Kaeriyama | G11B 5/105 29/603.12 |
| 2017/0169989 | A1* | 6/2017 | Leyte Guerrero | H01J 37/20 |

OTHER PUBLICATIONS

Em-TecVS42 compact dual action spring-loaded SEM sample vise, Technical Support Bulletin (Year: 2015).*
Physik Instrumente, "Microscope Universal Holder for Slides and Petri Dishes," May 21, 2015, www.physikinstrumente.com.
Alex Rich, "Stickvise the Low Profile PVC Vise," Oct. 19, 2016, web.archive.org/web/20161019201934/http:/www.stickvise.com.
Micro to Nano, "Technical Support Bulletin EM-Tec VS42 Universal Spring-loaded Vise," Dec. 5, 2015, www.microtonano.com.

* cited by examiner

*Primary Examiner* — Suman K Nath
(74) *Attorney, Agent, or Firm* — Leveque IP Law, P.C.; Andrew J. Harrington

(57) ABSTRACT

An adjustable fixture for holding a sample for inspection with a scanning acoustic microscope includes a first horizontal bar disposed on a first end of a frame, and a second horizontal bar disposed on a second end of the frame. The second horizontal bar may be engaged with the frame to be movable between the first end and the second end of the frame. The adjustable fixture may further include a side bar disposed on one or more of the first side and the second side of the frame, with an end of the second horizontal bar slidable and lockable along the side bar, and an engagement mechanism releasably coupling the end of the second horizontal bar to the side bar.

41 Claims, 22 Drawing Sheets

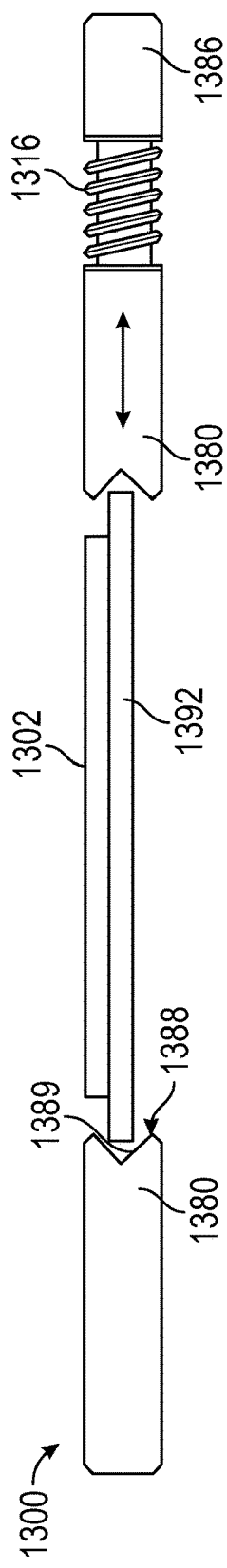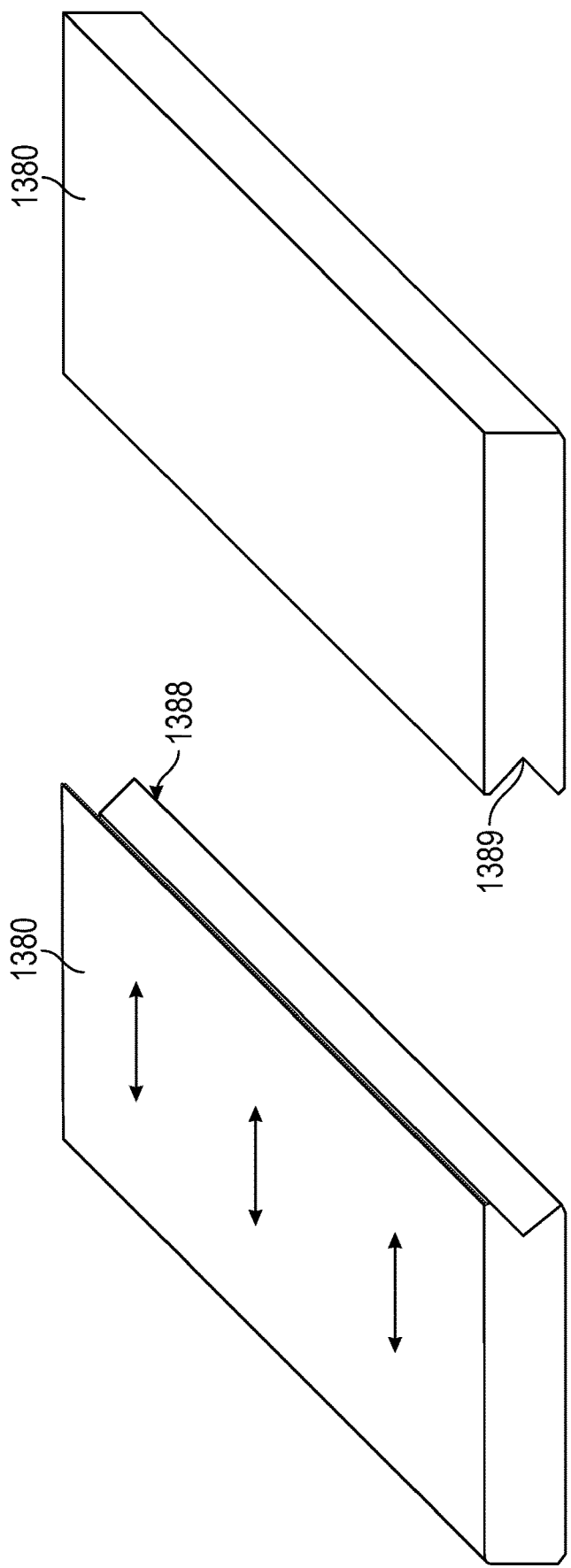
FIG. 13
FIG. 14

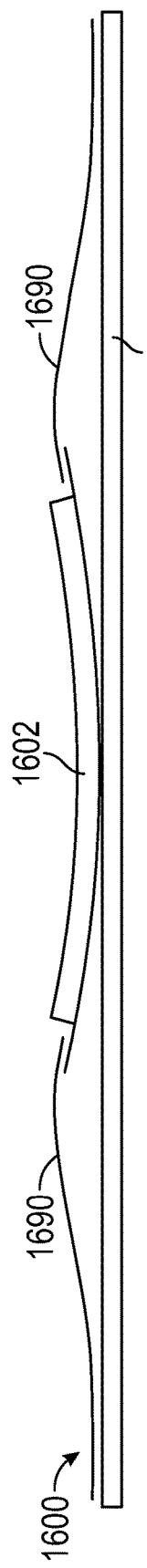
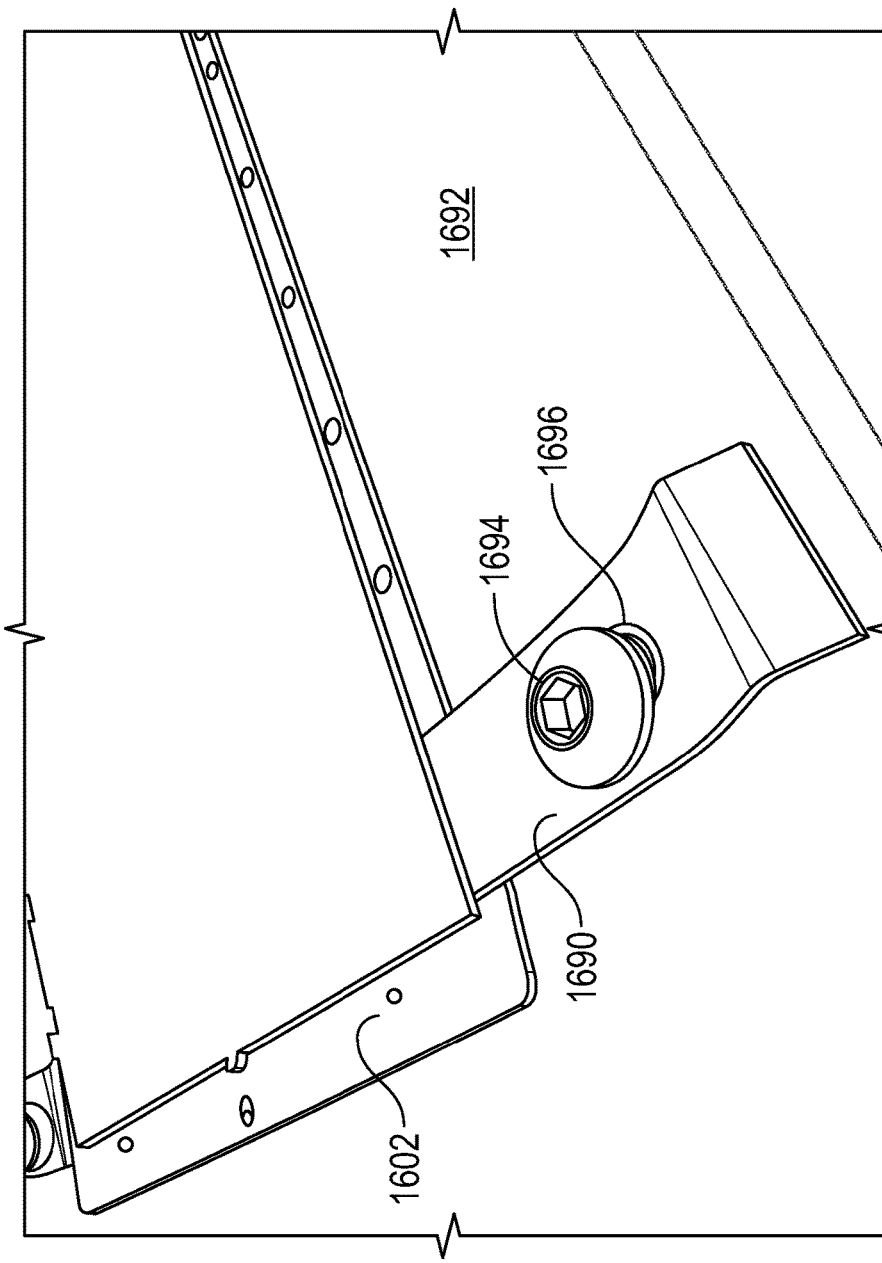

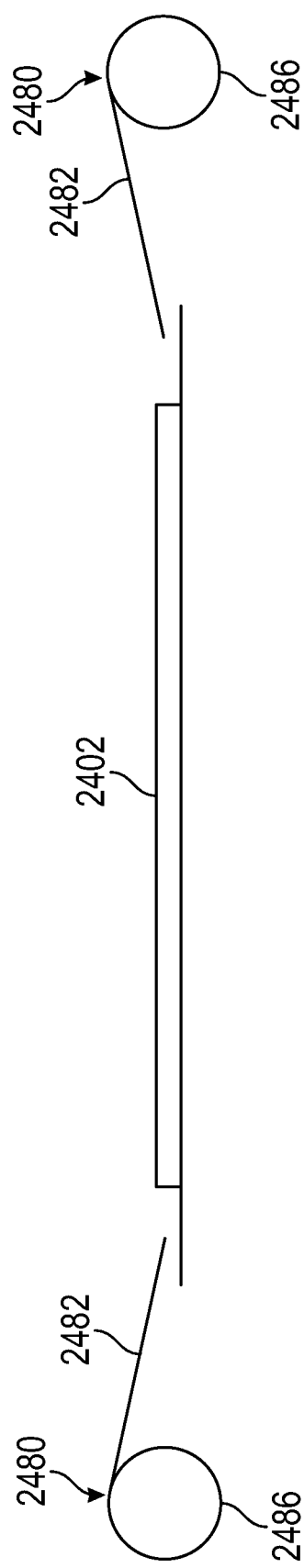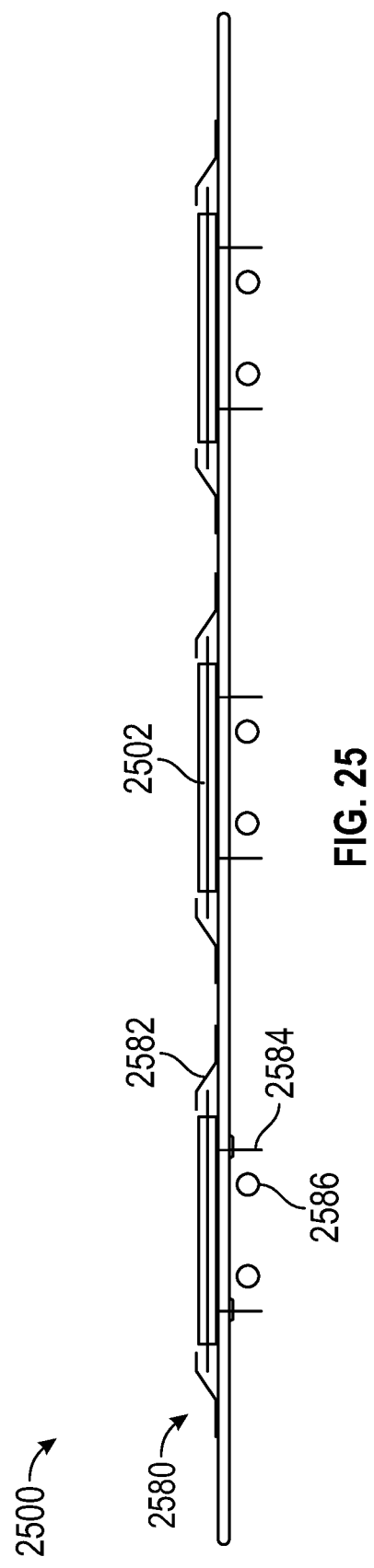

ADJUSTABLE FIXTURE FOR SCANNING ACOUSTIC MICROSCOPY

CROSS-REFERENCE TO RELATED APPLICATIONS

This application claims the benefit of U.S. Provisional Patent Application No. 62/417,482 filed on Nov. 4, 2016, the entire content of which is hereby incorporated by reference.

BACKGROUND

A scanning acoustic microscope may be used to produce scanned images of objects (which may be otherwise referred to herein as "samples") using ultrasound. In some scanning acoustic microscopes, the sample is held in place in a tank of fluid and insonified with pulses of ultrasound from a transmitting transducer at a number of locations in a scan pattern. To this end, a fixture is generally used to hold the sample in place.

A scanning acoustic microscope may thus be used to scan samples of different sizes and shapes, where a custom fixture is typically needed for each different sample. Therefore, a scanning acoustic microscope system or a user thereof may require many different fixtures, and changing from one custom fixture to another, which can reduce the time available for scanning as the fixtures are replaced and interchanged.

There remains a need for a fixture capable of holding samples of different sizes and shapes, e.g., to be inspected and scanned by a scanning acoustic microscope.

BRIEF DESCRIPTION OF THE DRAWINGS

The accompanying drawings provide visual representations which will be used to more fully describe various representative embodiments and can be used by those skilled in the art to better understand the representative embodiments disclosed and their inherent advantages. The drawings are not necessarily to scale, emphasis instead being placed upon illustrating the principles of the devices, systems, and methods described herein. In these drawings, like reference numerals may identify corresponding elements.

FIG. 13 illustrates an adjustable fixture holding a sample, in accordance with a representative embodiment.

FIG. 14 illustrates clamp jaws of an adjustable fixture, in accordance with a representative embodiment.

FIG. 16 illustrates an adjustable fixture holding a sample, in accordance with a representative embodiment.

FIG. 17 is a photograph of a clamp of an adjustable fixture, in accordance with a representative embodiment.

FIG. 24 illustrates spring clamps of an adjustable fixture, in accordance with a representative embodiment.

FIG. 25 illustrates clamps of an adjustable fixture, in accordance with a representative embodiment.

DETAILED DESCRIPTION

Figure 1:
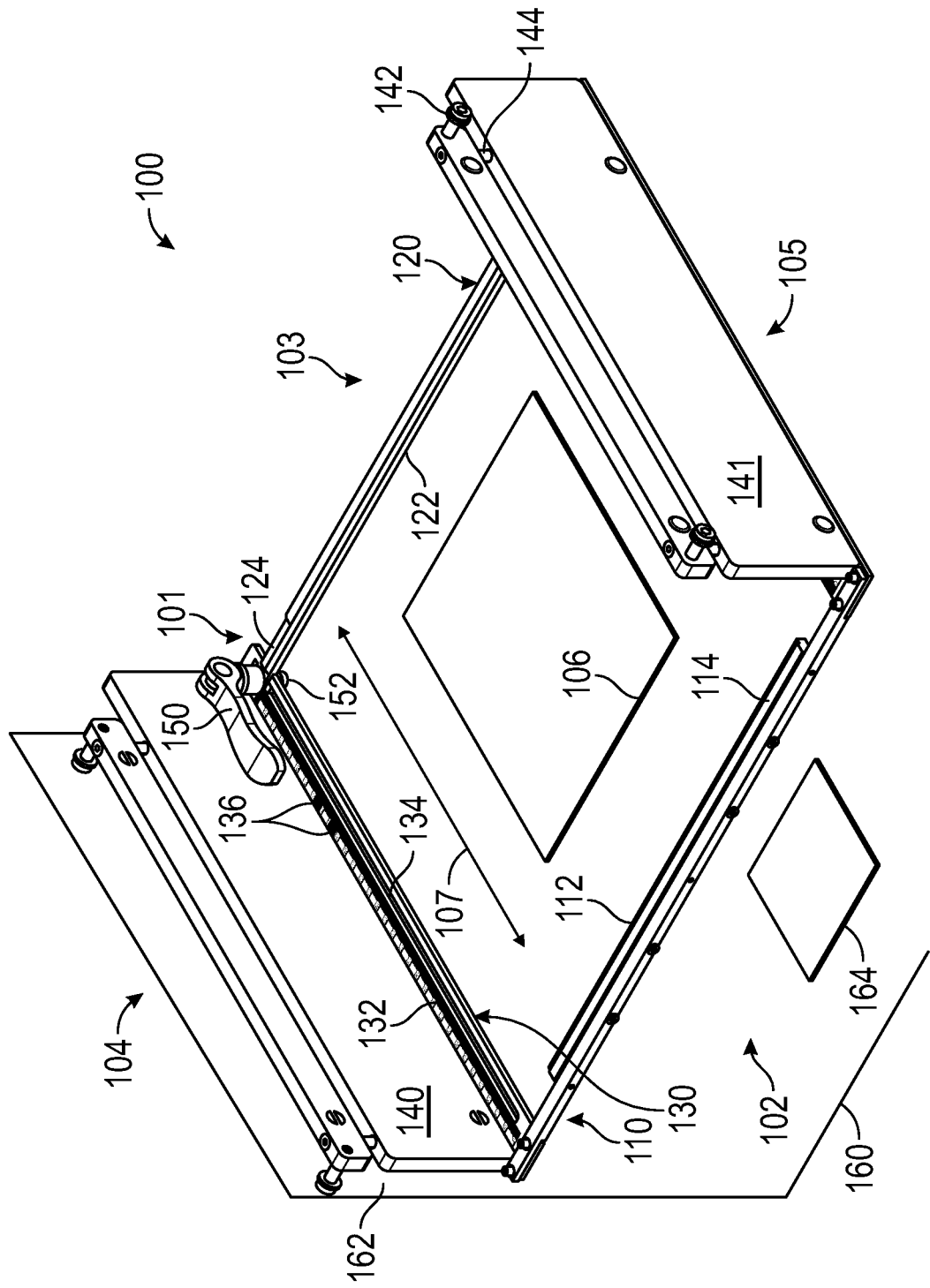
FIG. 1 illustrates an adjustable fixture, in accordance with a representative embodiment.

The various methods, systems, apparatuses, and devices described herein generally include holding and securing samples in a scanning acoustic microscope for inspection of the samples.

While this invention is susceptible of embodiment in many different forms, there is shown in the drawings and will herein be described in detail specific embodiments, with the understanding that the present disclosure is to be considered as an example of the principles of the invention and not intended to limit the invention to the specific embodiments shown and described. In the description below, like reference numerals may be used to describe the same, similar or corresponding parts in the several views of the drawings.

In this document, relational terms such as first and second, top and bottom, and the like may be used solely to distinguish one entity or action from another entity or action without necessarily requiring or implying any actual such relationship or order between such entities or actions. The terms "comprises," "comprising," "includes," "including," "has," "having," or any other variations thereof, are intended to cover a non-exclusive inclusion, such that a process, method, article, or apparatus that comprises a list of elements does not include only those elements but may include other elements not expressly listed or inherent to such process, method, article, or apparatus. An element preceded by "comprises . . . a" does not, without more constraints, preclude the existence of additional identical elements in the process, method, article, or apparatus that comprises the element.

Reference throughout this document to "one embodiment," "certain embodiments," "an embodiment," "implementation(s)," "aspect(s)," or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means "any of the following: A; B; C; A and B; A and C; B and C; A, B and C." An exception to this definition will occur only when a combination of elements, functions, steps or acts are in some way inherently mutually exclusive. Also, grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth.

All documents mentioned herein are hereby incorporated by reference in their entirety. References to items in the singular should be understood to include items in the plural, and vice versa, unless explicitly stated otherwise or clear from the text.

Recitation of ranges of values herein are not intended to be limiting, referring instead individually to any and all values falling within the range, unless otherwise indicated, and each separate value within such a range is incorporated into the specification as if it were individually recited herein. The words "about," "approximately," or the like, when accompanying a numerical value, are to be construed as indicating a deviation as would be appreciated by one of ordinary skill in the art to operate satisfactorily for an intended purpose. Ranges of values and/or numeric values are provided herein as examples only, and do not constitute a limitation on the scope of the described embodiments. The use of any and all examples, or exemplary language ("e.g.," "such as," or the like) provided herein, is intended merely to better illuminate the embodiments and does not pose a limitation on the scope of the embodiments. No language in the specification should be construed as indicating any unclaimed element as essential to the practice of the embodiments.

For simplicity and clarity of illustration, reference numerals may be repeated among the figures to indicate corresponding or analogous elements. Numerous details are set forth to provide an understanding of the embodiments described herein. The embodiments may be practiced without these details. In other instances, well-known methods, procedures, and components have not been described in detail to avoid obscuring the embodiments described. The description is not to be considered as limited to the scope of the embodiments described herein.

In the following description, it is understood that terms such as "first," "second," "top," "bottom," "up," "down," "above," "below," and the like, are words of convenience and are not to be construed as limiting terms. Also, the terms apparatus and device may be used interchangeably in this text.

A scanning acoustic microscope may image objects using ultrasound. In some scanning acoustic microscopes, the object is held in place in a tank of fluid and insonified with pulses of ultrasound from a transmitting transducer at a number of locations. The reflected and transmitted ultrasound may be sensed at a receiving transducer and analyzed to form an image of the object. The fluid in the tank may couple the ultrasound between the object and the transducer.

In general, the devices, systems, and methods described herein may include an adjustable fixture, or the use of an adjustable fixture, for holding and securing objects for inspection using a scanning acoustic microscope or the like. It will be understood that any reference to one or more of supporting, stabilizing, holding, securing, and similar terms when discussing the adjustable fixture, will be understood to include any and all such terms unless explicitly stated to the contrary or otherwise clear from the context. Further, any reference to one or more of scanning, inspection, measuring, analyzing, imaging, and the like (e.g., by a scanning acoustic microscope), will be understood to include any and all such terms unless explicitly stated to the contrary or otherwise clear from the context. Thus, although the disclosure may refer to "scanning," "imaging," or "inspection" using a scanning acoustic microscope, the techniques described herein may be used for other functions of a scanning acoustic microscope or similar devices in which a sample is held for analysis. In this manner, it will be understood that references in this disclosure to the use of the adjustable fixture with a "scanning acoustic microscope," may also or instead include use by similar devices unless explicitly stated to the contrary or otherwise clear from the context.

An object to be scanned is generally referred to herein as a "sample," which will be understood to include any object or item to be held for inspection, scanning, or imaging using a scanning acoustic microscope or the like, where the "sample" may include a single object, a single object in a holder (e.g., a frame, an adapter plate, a support surface, and the like), multiple objects, or multiple objects in a holder. The samples described herein may also or instead include Joint Electron Device Engineering Council (JEDEC) trays, strip samples, wafer samples, board samples, and combinations thereof.

As described herein, the present teachings include an adjustable fixture for a scanning acoustic microscope that can be adjusted for holding samples and sample holders of different types, sizes, shapes, weights, and so on, for inspection by the scanning acoustic microscope. For example, the adjustable fixture may be adjusted for holding single microelectronic packages, tray holders of microelectronic packages (such as, for example, tray holders that conform to a JEDEC standard), various sized boat holders of microelectronic packages, various sized microelectronic strips, various sized microelectronic wafers and bonded wafers (e.g., up to 300 mm in diameter, either on their own or in a wafer holder), and so on. The adjustable fixture may allow for either or both pulse echo (PE) and through transmission (TT) inspection modes on various sample types, where the adjustable fixture can hold a sample still, and can minimize warpage of a sample for improved inspection. An adjustable fixture of the present teachings may secure a sample at its edges, such that the area under the sample is substantially clear, where "substantially clear" will be understood to include a condition where the sample can be properly inspected via a scanning acoustic microscope. In this manner, the adjustable fixture may allow for TT inspection of an almost infinite number of sample types. In addition, securing the sample at its edges may include having a component of the adjustable fixture extend only minimally above the sample edge, if at all, e.g., such that there is a limited risk of collision between the ultrasonic transducer and the adjustable fixture.

Other fixtures of the prior art may have significant limitations relative to the present teachings, where several other fixtures of the prior art are discussed below by way of example.

JEDEC tray-sized fixtures have been used in the art. That is, one of the most common type of fixtures in the art includes a rectangular frame with sliding C-clamps that are adjusted to match the x-dimension of a JEDEC tray, where the y-dimension is fixed to the y-dimension of the JEDEC tray. Such JEDEC tray-sized fixtures were useful because, initially, scanning acoustic microscopes were used for inspecting finished microelectronic packages. Typically, these units were transported in JEDEC trays, which follow JEDEC guidelines for the outer dimensions of the tray, but can have a variety of inner dimensions to properly fit the particular microelectronic packages. A JEDEC tray with at least some microelectronic packages was then loaded into a scanning acoustic microscope for the samples to be inspected.

In some cases, individual parts that were not in a JEDEC tray were also inspected. This was typically done by using a JEDEC-sized plate that fits into a JEDEC tray-sized fixture, where the sample(s) were placed on the plate for inspection. In such cases, double-sided tape was often used to fix the samples in place for inspection. However, for TT inspection, the tape would often impede the propagation of the ultrasound, so the sample(s) had to be placed on the edge of the double-sided tape, or placed between two right-angle rulers to limit side-to-side motion. Initially, a plastic plate was used, thicker for PE and thinner for TT (to minimize attenuation effects), but over time the plastic plate can absorb water and become warped. A stainless-steel plate with gridlines was used for PE to better maintain flatness, but the stainless-steel plate does not allow for a TT signal to reach the receiver, so the plastic plate was still used for TT inspection.

In further cases, samples were transported in boats rather than JEDEC trays. These boats would vary in size, but prior art fixtures designed for JEDEC trays may only be used with JEDEC tray-sized boats. The limitations of this approach may include that: (a) the fixture is not designed to minimize warpage of JEDEC trays or sample plates; (b) a specific double-sided tape must be used to maintain adhesion in water, but leave no residue on samples; (c) if rulers are used to hold samples, there may still be some 'wiggle room' or slack, necessitating slower scan speeds and decreased throughput; and (d) boats may be limited to JEDEC tray dimensions.

Strip samples are used in the art. As the use of scanning acoustic microscopes matured in the microelectronic industry, it became desirable to inspect samples at earlier stages in the production process. One such earlier stage is when the samples are in strip form, i.e., the samples have not been separated into individual packages. Instead, the samples are combined on a strip of substrate material and may or may not have been over-molded. The strip dimensions can vary widely and the substrate material may be flexible making it difficult to maintain sample flatness across the whole strip.

In one prior art approach, the strips are simply placed on a JEDEC tray-sized plate for inspection, assuming that the strip is smaller than a JEDEC tray. A challenge with this approach may include that, if double-sided tape is used to hold the strip in place, when the strip is removed from the tape, the strip tends to curl up. And using less tape at the edges tends to limit the amount of flattening that can be applied to the strip during inspection. Consequently, only smaller sections of the strip are typically able to be done at one time using this technique. Further, if the tape was not used, the strips could either curl up, rock back and forth during scanning, or otherwise move during scanning. A further limitation of this approach is that the tape or plate may limit TT inspection capability.

Another approach includes the inspection of wafer samples using a wafer chuck or the like. That is, microelectronic samples can be inspected when they are still in the wafer state, e.g., as wafer samples. Wafer samples may include bonded wafers for inspection using a scanning acoustic microscope. In this manner, scanning systems may be present in a front-end fabrication environment used for bonded wafer inspection. A standard approach may be to use a wafer chuck or the like to hold a wafer sample flat. The wafer chuck can be metal or ceramic, with various hole patterns, suction cups, posts, and porous material approaches. Wafer chucks tend to hold a wafer sample with minimum contamination to the wafer sample itself. On these systems, a pressurized film of water in the area of inspection may be used to limit water contact. However, some types of wafer warpage may be difficult to pull flat or make a sufficient connection thereto. Also, TT inspection may not be possible with a wafer chuck. Also, in a laboratory or research and development environment, there is often insufficient volume to necessitate a fully automated system and, in many cases, wafer samples are not the only samples being inspected. A wafer chuck still remains a common approach even though TT may not generally be possible. Thus, in order to switch between sample types, the wafer chuck may be fully removed from the tank to be replaced by an alternate fixture that is then leveled. Further, a water bath may be needed for various strips and packages of samples. For example, if TT is required on wafer samples, a water bath may be needed and the wafers may be balanced on at least two JEDEC tray-sized fixtures. Alternatively, the wafer samples may be placed in a wafer holder that is then balanced on at least two JEDEC tray-sized fixtures. The limitations of this approach may include that the wafer sample can move during scanning, and support bars in the fixture may scatter the ultrasound producing shadows in the TT image that can hide potential defects in the sample.

Another approach includes the inspection of board samples. Thus, another sample type that may be inspected may include a populated or unpopulated printed circuit board (PCB). This inspection usually entails looking for a delamination within the layers of the board sample. The most common approach is to use TT inspection to look for defects in any layer. If specific layer information is needed, then pulse echo (PE) inspection may be used. If the board samples are smaller than a JEDEC tray, they may be placed on a standard JEDEC tray-sized fixture. However, it may be difficult to fix samples in place, which can result in movement during scanning. If the board samples are larger than a JEDEC tray, then samples tend to be balanced on one or two JEDEC tray-sized fixtures, as in the wafer case discussed above, which has similar limitations.

Other approaches for holding different sized samples have been tried previously, but have also had significant limitations. Several such approaches are discussed below.

In a first approach, a metal frame is placed on top of a strip sample with y-direction frame lines and set so that it is between device array sections on the strip sample. However, because the thickness of the metal frame cannot exceed the height of the device or there may be a collision risk, this limits the weight of the metal frame and its ability to flatten and hold the strip sample in place. Further, a different frame would be needed for each strip layout. And, for TT inspection, the plate underneath may limit the TT signal.

A second approach uses a magnetized plate under the sample. In some cases, the strip substrate is able to be pulled flat by the magnetic force of the substrate, but in some cases, a metal frame that is attracted to the magnet is used to try and further flatten the strip. However, only some strip samples are sufficiently attracted to the magnet and, further, the limitations on frame thickness and the need to have a different frame for each strip layout are still present. Also, the magnetized plate does not allow for TT inspection.

A third approach is to lay a frame with wires in a mesh pattern on top of a strip sample to pull the strip flat. However, a difficulty with this approach may include that the wires scatter the ultrasound, which can lead to shadows in sample images (using both PE and TT) that hide regions of the device. Thus, it may not be possible to know whether a defect is present in areas disposed under the wires. Also, there may be a risk of collision between the wires and the transducer.

A fourth approach is to use a vacuum chuck to pull a strip sample flat. Versions of this approach may use a standard vacuum as well as the Bernoulli effect (with air or water motion). This approach does tend to pull the strip flat, but it may be expensive, require a way to separate water and air in the vacuum lines, tend to require a way to lift the fixture out of the water to affix the sample, and provide no way to conduct TT inspection.

A fifth approach is to use clips to hold a strip sample flat against the support plate. The clips may be rotated into position and then tightened down, or a type of spring clip may be used to hold, release, and change samples. Drawbacks of this approach may include that the clips cannot be located any higher than the height of the strip sample to avoid collisions, which limits the amount of force that can be used to flatten the strip sample. Further, changing a sample may take several motions for each clip, thus making this approach user intensive and time consuming. Also, metal clips can scratch or damage a strip sample, and a support plate may not allow for TT scanning.

Therefore, devices, systems, and methods according to the present teachings may be desirable to overcome the above-identified deficiencies. More specifically, an adjustable fixture as described herein may overcome the above-identified deficiencies.

In certain implementations, an adjustable fixture operates by the use of at least two horizontal bars, e.g., a first horizontal bar and a second horizontal bar, where one or more is movable with respect to the other. For example, a second horizontal bar may be adjusted to a position according to a size of the sample to be inspected, and a spring-loaded first horizontal bar may allow the sample to be loaded and hold the sample firmly in place. Once the second horizontal bar is in position, multiple samples may be loaded quickly and easily by slotting a sample into a groove or the like disposed in the first horizontal bar (e.g., a "v-groove"), pressing the first horizontal bar against a spring element to allow a side of the sample to be loaded into a corresponding groove or the like disposed in the second horizontal bar (e.g., a "v-groove"), and then releasing the first horizontal bar thereby pressing the sample into place between the first and second horizontal bars. In addition to holding the sample, this configuration may assist in flattening warpage of the sample.

Additional features for the adjustable fixture may include "quick-release" cam levers or the like for ease of moving the horizontal bars to a desired position according to the sample to be secured, grid lines or the like for ease of targeting the appropriate setting of the horizontal bars for different sample types, leveling screws or the like to align the adjustable fixture with a scanning plane, side pins or the like to lock the adjustable fixture against tank walls of a scanning acoustic microscope and to maintain alignment of the adjustable fixture, and a locator mechanism (e.g., a pin, a clamp, or the like) on a horizontal bar to ensure sample positioning.

FIG. 1 illustrates such an adjustable fixture 100, in accordance with a representative embodiment, e.g., an adjustable fixture 100 for holding a sample for inspection with a scanning acoustic microscope 160. The adjustable fixture 100 may include a frame 101, horizontal bars (e.g., a first horizontal bar 110 and a second horizontal bar 120), one or more side bars 130, side walls (e.g., a first side wall 140 and a second side wall 141), and an engagement mechanism 150.

The adjustable fixture 100 may be structurally configured to secure a sample at its edges (and nowhere else), or substantially at its edges, such that the area under the sample (the underside of the sample) is clear and unobstructed for inspection with a scanning acoustic microscope 160 or the like. In this manner, securing or holding the sample substantially at or along its edges may allow for TT inspection of various types of samples. In addition, securing or holding the sample substantially at or along its edges may result in having portions of the adjustable fixture 100 only extending minimally above the sample edge such that there is a limited risk of collision between the ultrasonic transducer of a scanning acoustic microscope 160 and portions of the adjustable fixture 100. Also, or instead, no portion of the adjustable fixture 100 may protrude above the sample (over the sample) so as to interfere with scanning. In general, the adjustable fixture 100 may operate by adjusting one or more of the horizontal bars to a desired position for the sample to be inspected, where one or more of the horizontal bars is spring loaded to allow the sample to easily be loaded and to hold the sample firmly in place within the adjustable fixture 100.

The frame 101 may include a first end 102, a second end 103, a first side 104, and a second side 105. The frame 101 may be made from materials that provide sufficient stability to support a sample, including without limitation metal, ceramic, plastic, composites, and combinations thereof.

The horizontal bars may include a first horizontal bar 110 and a second horizontal bar 120. In general, and as described below, at least one of the horizontal bars may be movable for adjustment to secure a sample on the adjustable fixture 100. Also, or instead, at least one of the horizontal bars may be spring loaded. Although generally adjustable fixtures 100 with two horizontal bars are shown, it will be understood that more horizontal bars are possible. For example, an alternate adjustable fixture may include three horizontal bars, where a first sample may be held between a first and second horizontal bar, and a second, distinct sample may be held between a second and third horizontal bar.

The first horizontal bar 110 may be disposed on the first end 102 of the frame 101, and the second horizontal bar 120 may be disposed on the second end 103 of the frame 101. The first horizontal bar 110 may include a first face 112 structurally configured for engagement with a first end of a sample, and the second horizontal bar 120 may include a second face 122 opposing the first face 112, where the second face 122 is structurally configured for engagement with a second end of the sample. Thus, the first face 112 and the second face 122 may generally include opposing surfaces structurally configured to engage with the sample. As described in more detail below, the second horizontal bar 120 may be engaged with the frame 101 to be movable between the first end 102 and the second end 103 of the frame 101.

The adjustable fixture 100 may include one or more side bars 130. A side bar 130 may be disposed on one or more of the first side 104 and the second side 105 of the frame 101. An end of the second horizontal bar 120 (e.g., one or more of a first end 124 thereof and a second end 326 thereof—see FIG. 3 described below) may be slidable and lockable along the side bar 130. To this end, the adjustable fixture 100 may include an engagement mechanism 150 releasably coupling an end of the second horizontal bar 120 (e.g., one or more of a first end 124 thereof and a second end 326 thereof—see FIG. 3 described below) to the side bar 130. It will be understood that the term "lock" and the like, as well as variations thereof, as used throughout this disclosure, shall include a releasable coupling or securing, e.g., where one component remains sufficiently coupled or secured in a releasable manner relative to another component for an intended purpose, such as inspection via a scanning acoustic microscope 160.

As discussed above, at least one of the horizontal bars may be spring loaded. For example, the first horizontal bar 110 may be spring loaded via one or more spring elements. In this manner, the first face 112 may be movable toward the first end 102 of the frame 101 when a force greater than a spring force of the spring elements is applied thereto. The spring force may be selected to allow the first face 112 to move toward the first end 102 of the frame 101 when receiving the first end of the sample. Also, or instead, the spring force may be selected to secure the sample on the frame 101 when the second end of the sample is engaged with the second face 122 of the second horizontal bar 120.

To facilitate a spring-loaded horizontal bar, support members may be connected to one or more of the horizontal bars, where one or more of the support members and the horizontal bars are movable relative to one another. For example, the adjustable fixture 100 may include a first support member 114 engaged to the first horizontal bar 110 via the one or more spring elements and movable relative to the first horizontal bar 110 via a predetermined spring force applied thereto. The first face 112 may thus be disposed on the first support member 114. Stated otherwise, the first support member 114 may include the first face 112, where the first face 112 is structurally configured for engagement with the first end of the sample.

One or more of the horizontal bars may include a groove. For example, the first horizontal bar 110 may include a first groove on the first face 112, and the second horizontal bar 120 may include a second groove on the second face 122. One or more of the first groove and the second groove may be tapered. In certain implementations, the tapering of one or more of the first groove and the second groove is structurally configured to flatten warpage of a sample when the sample is secured between the first horizontal bar 110 and the second horizontal bar 120.

As discussed above, one or more of the horizontal bars may be movable. For example, certain implementations include an adjustable fixture 100 where the first horizontal bar 110 is fixed on the first end 102 of the frame 101, and the second horizontal bar 120 is movable. In other implementations, each of the first horizontal bar 110 and the second horizontal bar 120 is movable between the first end 102 and the second end 103 of the frame 101.

In certain implementations, one or more of the side bar 130, the first horizontal bar 110, and the second horizontal bar 120 includes one or more markings 132. For example, as shown in FIG. 1, the side bar 130 may include markings 132. The markings 132 may correspond to different sample types for configuring the adjustable fixture 100 to hold at least one of the different sample types. The markings 132 may include grid lines, measurements (e.g., ruler markings), text, illustrations, and the like, as well as combinations thereof. For example, the markings 132 on the side bar 130 may be used to maintain a parallel arrangement of the second horizontal bar 120 with the first horizontal bar 110.

The side bar 130 may include a slot 134. The slot 134 may be structurally configured for one or more of the horizontal bars to engage and slide therethrough between the first end 102 and the second end 103 of the frame 101. To this end, the adjustable fixture 100 may include a protuberance 152 disposed on one or more of the engagement mechanism 150 and an end of one or more of the horizontal bars (e.g., the second horizontal bar 120), where the protuberance 152 is sized and shaped for engagement with the slot 134. The protuberance 152 may further be structurally configured to prevent rotation of one or more of the horizontal bars relative to the side bar 130, and to maintain a predetermined alignment of one or more of the horizontal bars relative to the side bar 130. For example, the protuberance 152 may be structurally configured to prevent rotation of the second horizontal bar 120 relative to the side bar 130, and to maintain a predetermined alignment of the second horizontal bar 120 with the first horizontal bar 110. To this end, the protuberance 152 may be extended along a first axis 107, which may prevent rotation of a horizontal bar. The protuberance 152 may also or instead help to maintain the second horizontal bar 120 parallel with the first horizontal bar 110.

The side bar 130 may also or instead include one or more notches 136 for positioning one or more of the horizontal bars relative to the side bar 130. For example, the notches 136 may be structurally configured for positioning the second horizontal bar 120 in predetermined locations between the first end 102 and the second end 103 of the frame 101. In certain implementations, one or more of the horizontal bars and the engagement mechanism 150 includes a component to engage with the notches 136 for positioning of a horizontal bar along the side bar 130.

The engagement mechanism 150 may work in conjunction with one or more of the horizontal bars and the side bar 130 for securing a position of a horizontal bar along the side bar 130. To this end, the engagement mechanism 150 may include a quick-release mechanism such as a quick-release lever, and more specifically a quick-release cam lever or the like, as shown in FIG. 1. The engagement mechanism 150 may also or instead include a thumbscrew. In general, the engagement mechanism 150 may include any mechanism or component for releasably securing or locking the position of a horizontal bar along the side bar 130.

The adjustable fixture 100 may further include side walls. Specifically, the adjustable fixture 100 may include a first side wall 140 disposed on the first side 104 of the frame 101, and a second side 141 wall disposed on the second side 105 of the frame 101. The side bar 130 may be supported by one or more of the first side wall 140 and the second side wall 141.

In certain implementations, each of the first side wall 140 and the second side wall 141 is sized and shaped for alignment with a wall 162 of an immersion tank of a scanning acoustic microscope 160. Thus, the adjustable fixture 100 may be sized and shaped to fit inside of an immersion tank, and can either be mounted to the bottom of the tank (which may be sloping) or to existing mounting points along the top of the immersion tank. The orientation of the adjustable fixture 100 may be adjustable so as to enable the adjustable fixture 100 to be leveled, for example. In this manner, alignment of each of the first side wall 140 and the second side wall 141 with the wall 162 of the immersion tank may be adjustable. To this end, one or more frame locking mechanisms 142 may be included on the side walls, e.g., where the frame locking mechanisms 142 are structurally configured to secure the frame 101 with a scanning acoustic microscope 160. For example, a frame locking mechanism 142 may be disposed on each of the first side wall 140 and the second side wall 141. The frame locking mechanisms 142 may include, e.g., one or more pins or the like. The frame locking mechanisms 142 may also or instead be separate from the side walls, and otherwise included on the frame 101. In either case, in general, the frame locking mechanisms 142 may be structurally configured to secure the frame 101 with the scanning acoustic microscope 160. The frame locking mechanisms 142 may also or instead allow for adjustment of an orientation of the frame 101 relative to the scanning acoustic microscope 160.

Also, or instead, the first side wall 140 and the second side wall 141 may be structurally configured to maintain a predetermined alignment between a sample plane 106 of the frame 101 and a scanning plane 164 of the scanning acoustic microscope 160, where the sample plane 106 of the frame 101 intersects both the first horizontal bar 110 and the second horizontal bar 120. The predetermined alignment may include a configuration where the sample plane 106 of the frame 101 is parallel to the scanning plane 164 of the scanning acoustic microscope 160.

The adjustable fixture 100 may further include one or more leveling elements 144 structurally configured to align the frame 101 with the scanning plane 164 of the scanning acoustic microscope 160. For example, the leveling elements 144 may include one or more leveling screws or the like.

Thus, in general, the adjustable fixture 100 may be structurally configured for easily and conveniently securing different sized and shaped samples therein for inspection. The adjustable fixture 100 may include features to this end, such as quick-release cam levers for ease of moving one or more of the horizontal bars to the correct position for a particular sample, grid lines or other markings 132 on the side bar 130 for ease of targeting an appropriate dimension for different sample types, leveling elements 144 (e.g., leveling screws) to align the frame 101 with a scanning plane 164, a frame locking mechanism 142 (e.g., side pins) to lock the adjustable fixture 100 against tank walls 162 and to maintain perpendicularity of the adjustable fixture 100 to a scanning tool, and sample locator mechanisms (e.g., locator pins as described herein) disposed on one or more of the horizontal bars to ensure proper positioning of the sample in the adjustable fixture 100.

Figure 2:
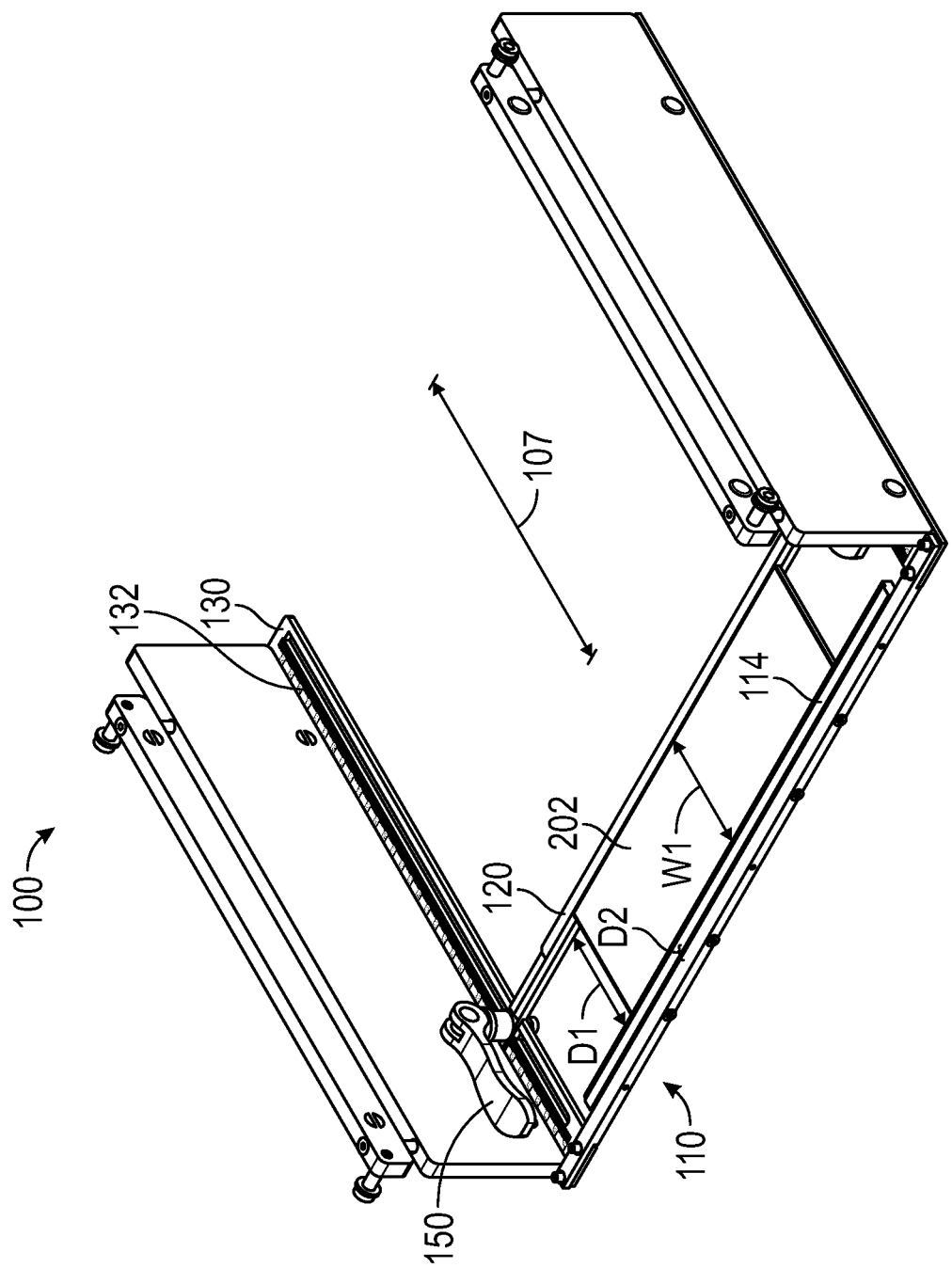
FIG. 2 illustrates an adjustable fixture holding a sample, in accordance with a representative embodiment.
Figure 3:
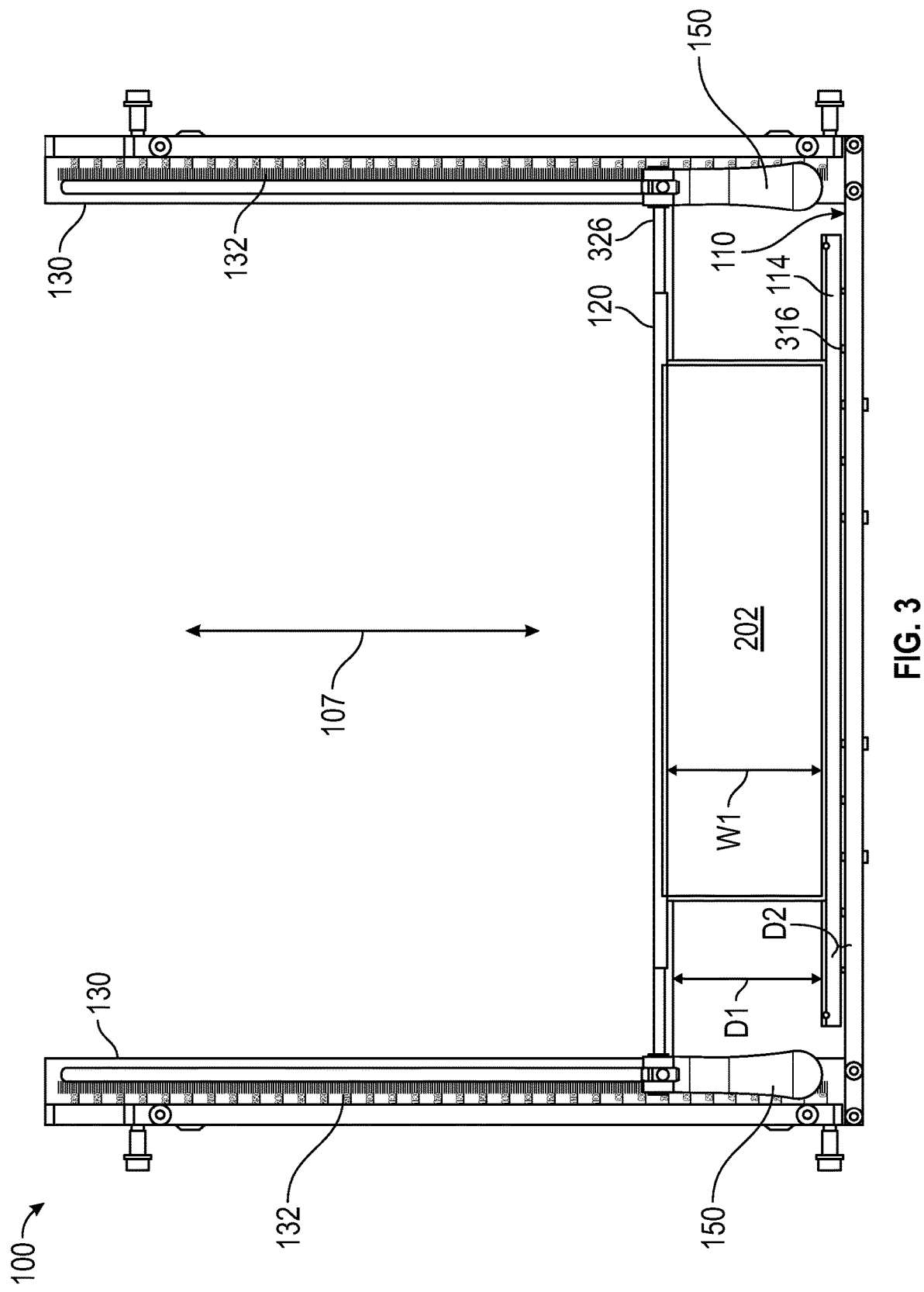
FIG. 3 illustrates a top view of the adjustable fixture of FIG. 2, in accordance with a representative embodiment.

FIG. 2 illustrates an adjustable fixture 100 holding a sample 202, in accordance with a representative embodiment, and FIG. 3 illustrates a top view of the adjustable fixture 100 shown in FIG. 2. The sample 202 shown in these figures may include a strip sample. As shown in the FIGS. 2 and 3, the adjustable fixture 100 may secure the sample 202 only at its edges so that the area under the sample 202 is clear, which can allow for TT inspection of the sample 202. In FIGS. 2 and 3, the second horizontal bar 120 has been moved forward along the first axis 107 to a position corresponding to the size and shape of the sample 202.

As shown in FIG. 3, the adjustable fixture 100 may include at least two side bars 130, where each may include markings 132 such as ruler measurements (in centimeters, millimeters, inches, or another appropriate unit of measurement). The adjustable fixture 100 may also include at least two engagement mechanisms 150, e.g., in the form of quick-release cam levers that are used to secure at least the second horizontal bar 120 to the side bars 130.

FIG. 3 also shows an example of a configuration for a spring-loaded horizontal bar, i.e., the first horizontal bar 110 in this example. As shown in the figure, spring elements 316 may be disposed between, and may connect, a first support member 114 to the first horizontal bar 110. The first support member 114 may be movable relative to the first horizontal bar 110, e.g., where the first support member 114 is structurally configured to move toward the first horizontal bar 110 against a predetermined spring force applied by the spring elements 316. In this manner, in certain implementations, the second horizontal bar 120 may be positioned along the first axis 107 such that the distance D1 between the second horizontal bar 120 and the face 112 of the first support member 114 is substantially equal to a width W1 of the sample 202. This distance D1 may be slightly increased, e.g., by a distance D2 (a distance between the first support member 114 and the first horizontal bar 110), through compression of the first support member 114 against the first horizontal bar 110 via compression of the spring elements 316. This may facilitate both placement of the sample 202 onto the adjustable fixture 100 and removal of the sample 202 from the adjustable fixture 100, e.g., while the second horizontal bar 120 and the first horizontal bar 110 are in fixed positions via a locking of the engagement mechanisms 150.

The spring elements 316, or any other springs or spring elements described herein, may include a biasing member such as any of a variety of springs and spring mechanisms. For example, a spring element 316 may include a coil spring, a leaf spring, or any other type of spring or combination of springs. Other biasing members may also or instead be utilized.

Figure 4:
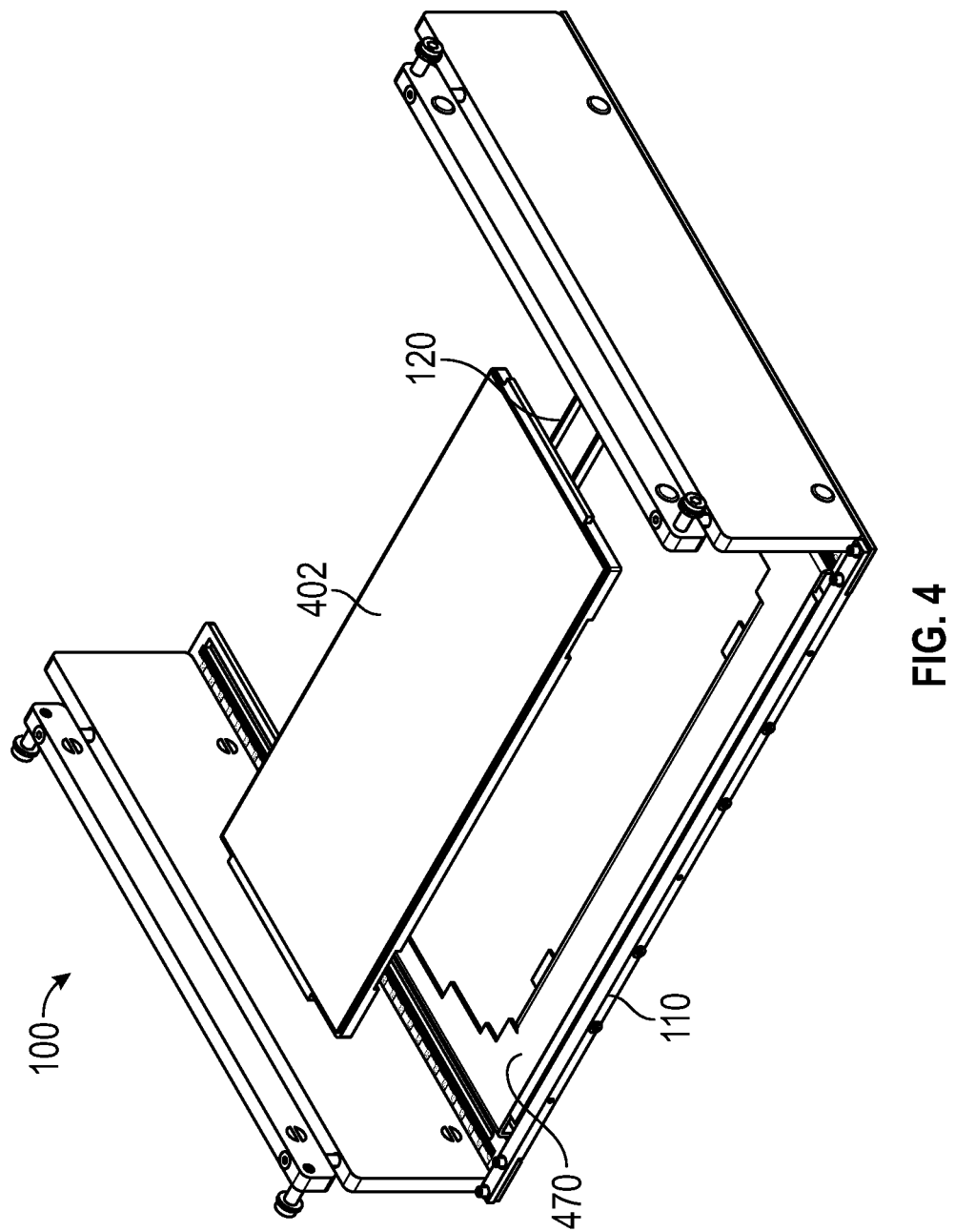
FIG. 4 illustrates an adjustable fixture receiving a sample, in accordance with a representative embodiment.
Figure 5:
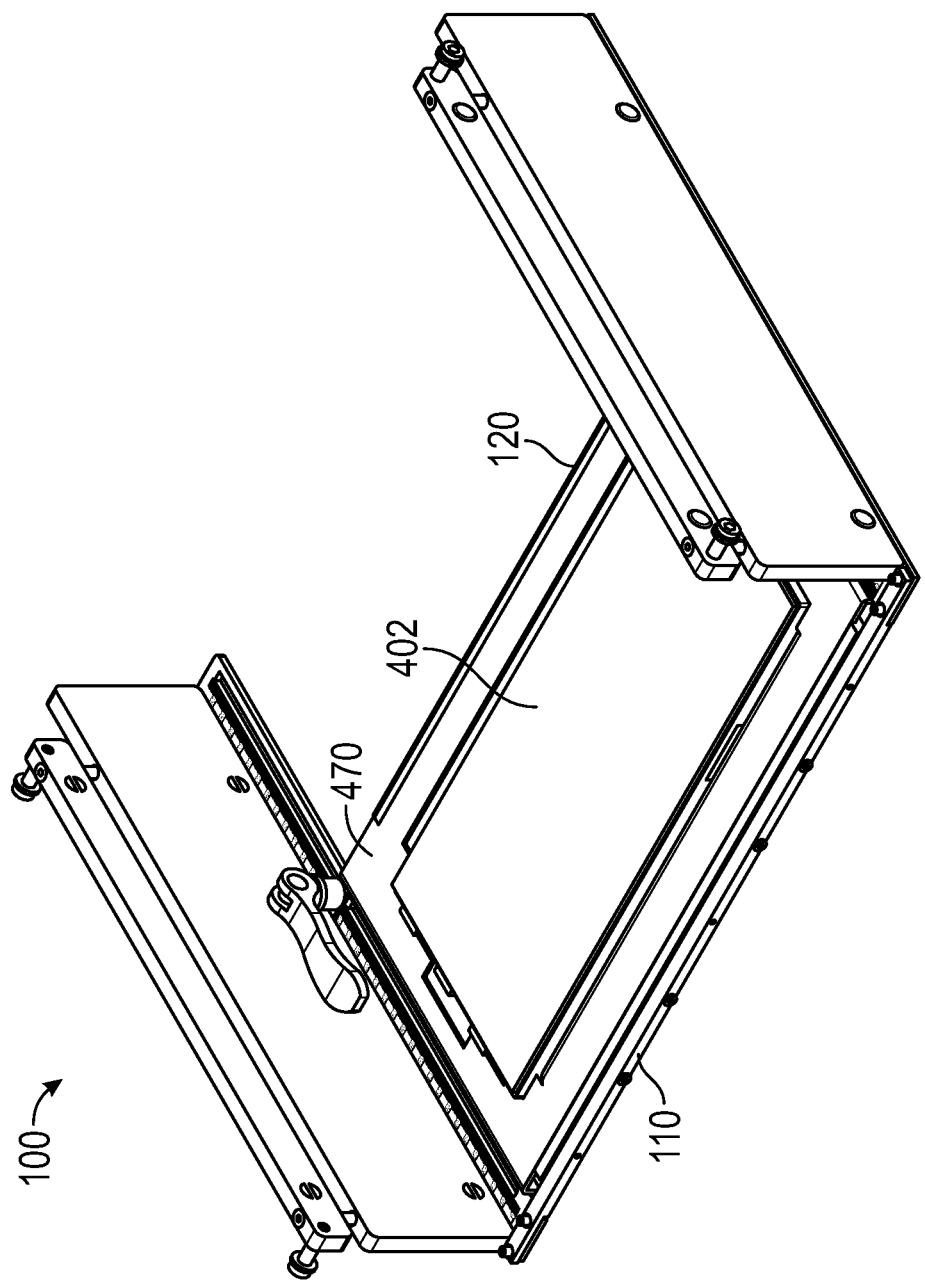
FIG. 5 illustrates an adjustable fixture holding a sample, in accordance with a representative embodiment.

FIG. 4 illustrates an adjustable fixture 100 receiving a sample 402, in accordance with a representative embodiment, and FIG. 5 illustrates the adjustable fixture 100 holding the sample 402. In these figures, the sample 402 may include a JEDEC tray or the like, where an adapter plate 470 is used to aid in securing the sample 402. Thus, in these figures, one or more of the first horizontal bar 110 and the second horizontal bar 120 may be adjusted to enable the adapter plate 470 to be placed therebetween, for holding a sample 402 for inspection with a scanning acoustic microscope or the like. Alternatively, the sample 402 may be held in the adjustable fixture 100 without the use of the adapter plate 470.

Thus, as shown in FIGS. 4 and 5, the adjustable fixture 100 may include an adapter plate 470 structurally configured for placement and securement between the first horizontal bar 110 and the second horizontal bar 120. The adapter plate 470 may be sized and shaped to hold a predetermined sample—including without limitation the sample 402 shown in the figures such as a JEDEC tray or the like, a wafer, a wafer holder, a strip sample, and so on.

In certain implementations, the adapter plate 470 may be metal, ceramic, glass, plastic, or a combination thereof. For example, samples 402 may be placed on an adapter plate 470 that includes a plastic baffle plate that provides support for the sample 402. In certain implementations, care should be taken to avoid trapping air between a sample 402 and the adapter plate 470, e.g., because trapped air may present an acoustic impedance mismatch that impairs TT scanning in a scanning acoustic microscope.

Figure 6:
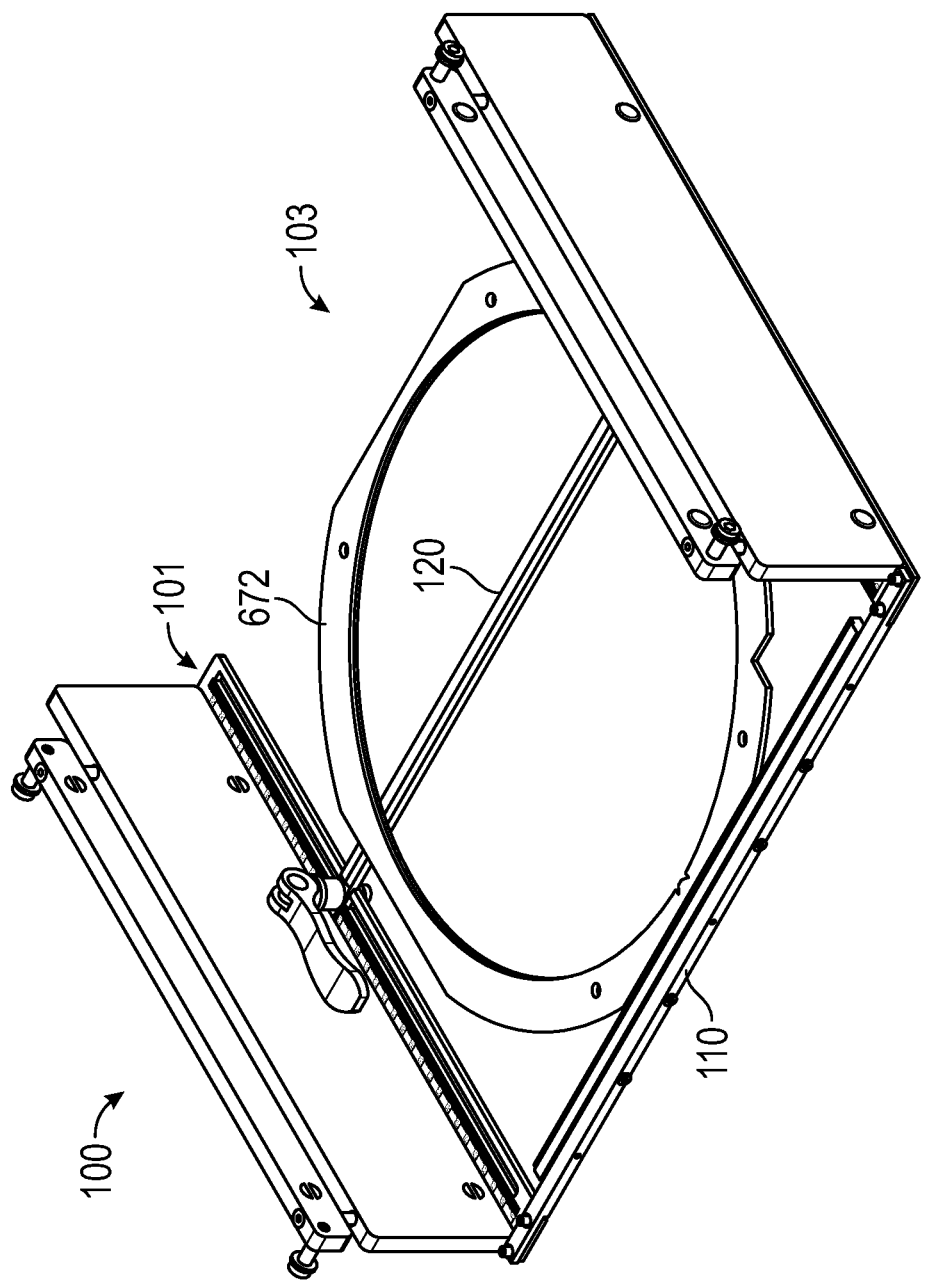
FIG. 6 illustrates an adjustable fixture with a wafer holder, in accordance with a representative embodiment.
Figure 7:
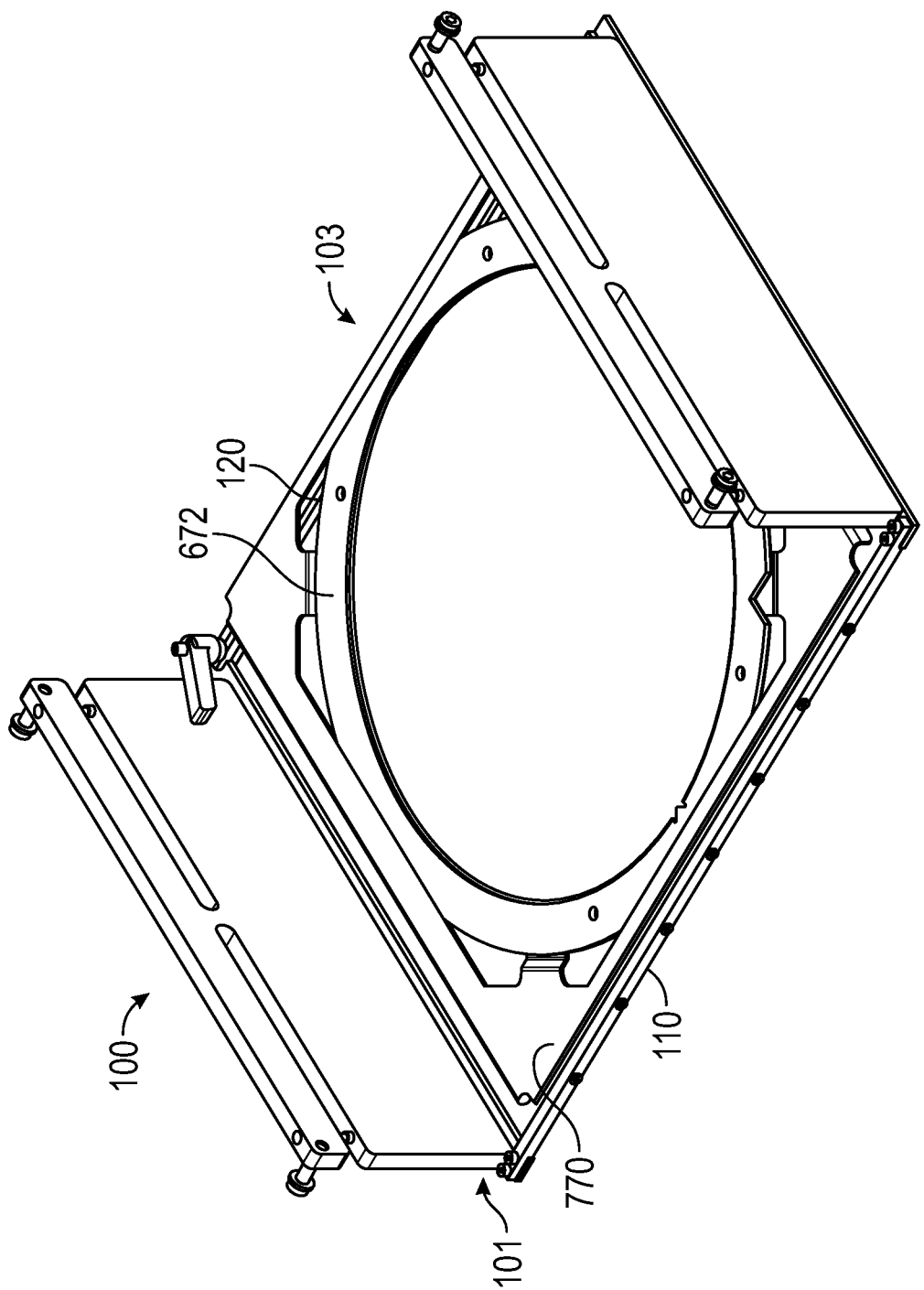
FIG. 7 illustrates an adjustable fixture with an adapter plater and a wafer holder, in accordance with a representative embodiment.

FIG. 6 illustrates an adjustable fixture 100 with a wafer holder 672, in accordance with a representative embodiment, and FIG. 7 illustrates the adjustable fixture 100 with an adapter plater 770 and a wafer holder 672. The wafer holder 672 may be structurally configured to hold, or otherwise support or engage, a sample in the form of a wafer or the like.

As shown in FIG. 6, the adjustable fixture 100 may be configured to engage a wafer holder 672, which may be supported by the first horizontal bar 110 and the second horizontal bar 120—e.g., being supported as shown in either or both of FIGS. 6 and 7. For example, the wafer holder 672 may be supported from underneath by one or more of the horizontal bars, the wafer holder 672 may be supported by being disposed between the horizontal bars, or the wafer holder 672 may be supported by an adapter plater 770. As such, FIG. 6 will be understood as depicting either (i) the wafer holder 672 being supported, or (ii) the adjustable fixture 100 before the second horizontal bar 120 is moved toward the second end 103 of the frame 101 for supporting the wafer holder 672 between the first horizontal bar 110 and the second horizontal bar 120.

As shown in FIG. 7, one or more of the first horizontal bar 110 and the second horizontal bar 120 is adjusted to enable an adapter plate 770 to be disposed and held therebetween, where the adapter plate 770 is structurally configured to support a wafer holder 672. Alternatively, the wafer holder 672, or even a wafer itself, may be held in the adjustable fixture 100 without the use of an adapter plate 770.

Figure 8:
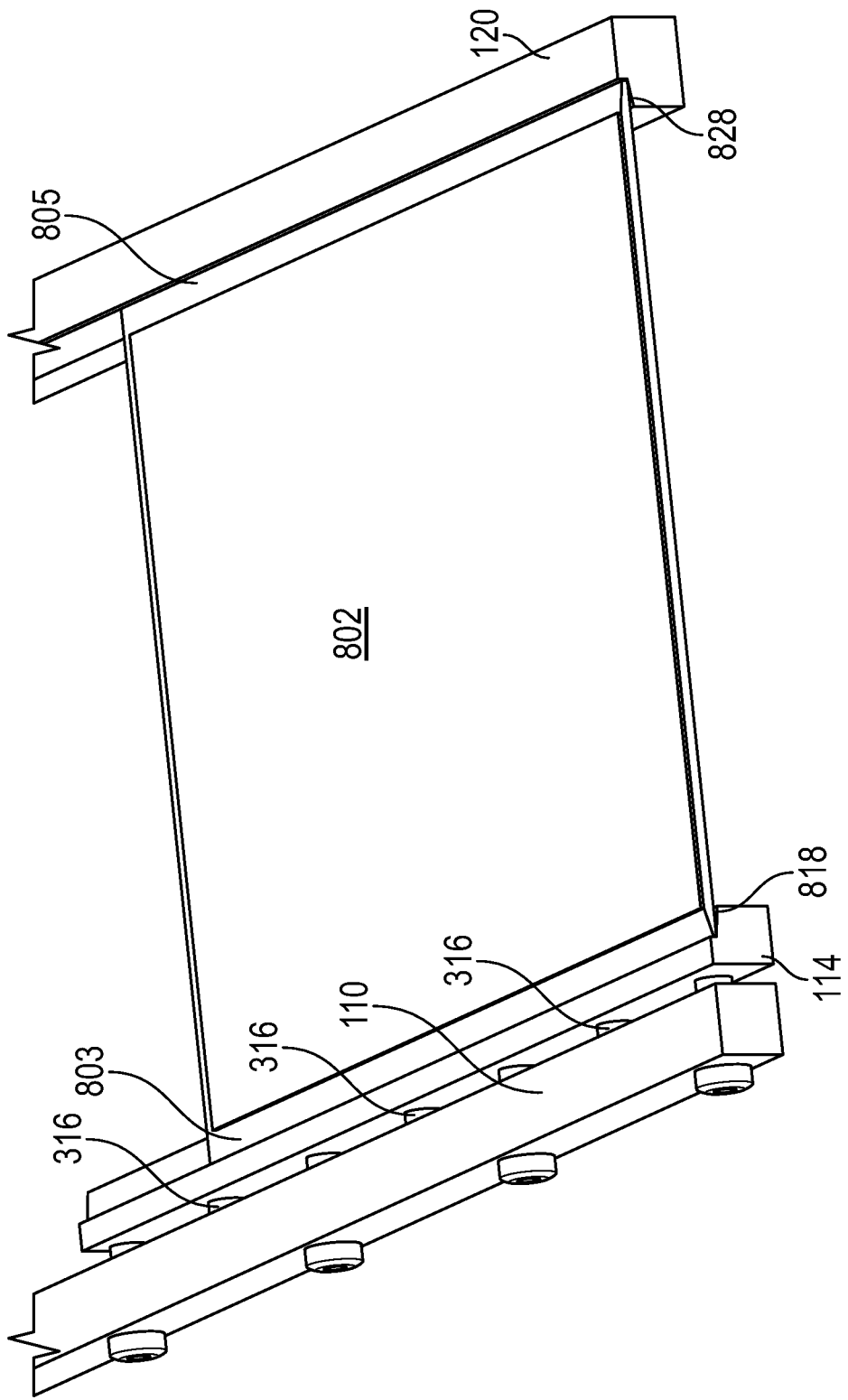
FIG. 8 illustrates a close-up view of a portion of an adjustable fixture holding a sample, in accordance with a representative embodiment.

FIG. 8 illustrates a close-up view of a portion of an adjustable fixture holding a sample 802, in accordance with a representative embodiment. Specifically, FIG. 8 shows an example of a first horizontal bar 110, a first support member 114, spring elements 316, a second horizontal bar 120, and a sample 802. The figure also shows an example of a first groove 818 on the first horizontal bar 110 and a second groove 828 on the second horizontal bar 120.

As shown in the figure, one or more of the first horizontal bar 110 and the second horizontal bar 120 may be adjusted to a predetermined position for the sample 802 to be inspected, e.g., by a scanning acoustic microscope. The first support member 114 may support one or more spring elements 316 located between first horizontal bar 110 and the first support member 114. The spring elements 316 may be compressed against a predetermined spring force to enable the sample 802 to be loaded into the first groove 818 of the first horizontal bar 110, and expanded to hold the sample 802 in a corresponding second groove 828 in the second horizontal bar 120. Thus, once the horizontal bars are in predetermined, proper positions, multiple samples 802 having generally the same size and shape may be loaded quickly and easily—e.g., by slotting a first end 803 of a sample 802 into the first groove 818 of the first horizontal bar 110, pressing the first support member 114 with at least the spring force against the spring elements 316 to allow a second end 805 of the sample to be loaded into the second groove 828 of the second horizontal bar 120, and then releasing the compression of the first support member 114 so the sample 802 is pressed into place between the horizontal bars. The first groove 818 and the second groove 828 may include a ledge that is disposed on the horizontal bars, the support members, or otherwise on the frame (e.g., a stepped surface). The first groove 818 and the second groove 828 may also or instead include a tapered or substantially "v-shaped" profile that can help flatten warpage of the sample 802, a slot, an indent, a cavity, a clearance, or combinations thereof. Grooves or slots with other profiles may also or instead be used. Further, although only a first support member 114 engaged with spring elements 316 is shown, another support member may also or instead be present—e.g., a second support member coupled with the second horizontal bar 120 via one or more spring elements 316.

Figure 9:
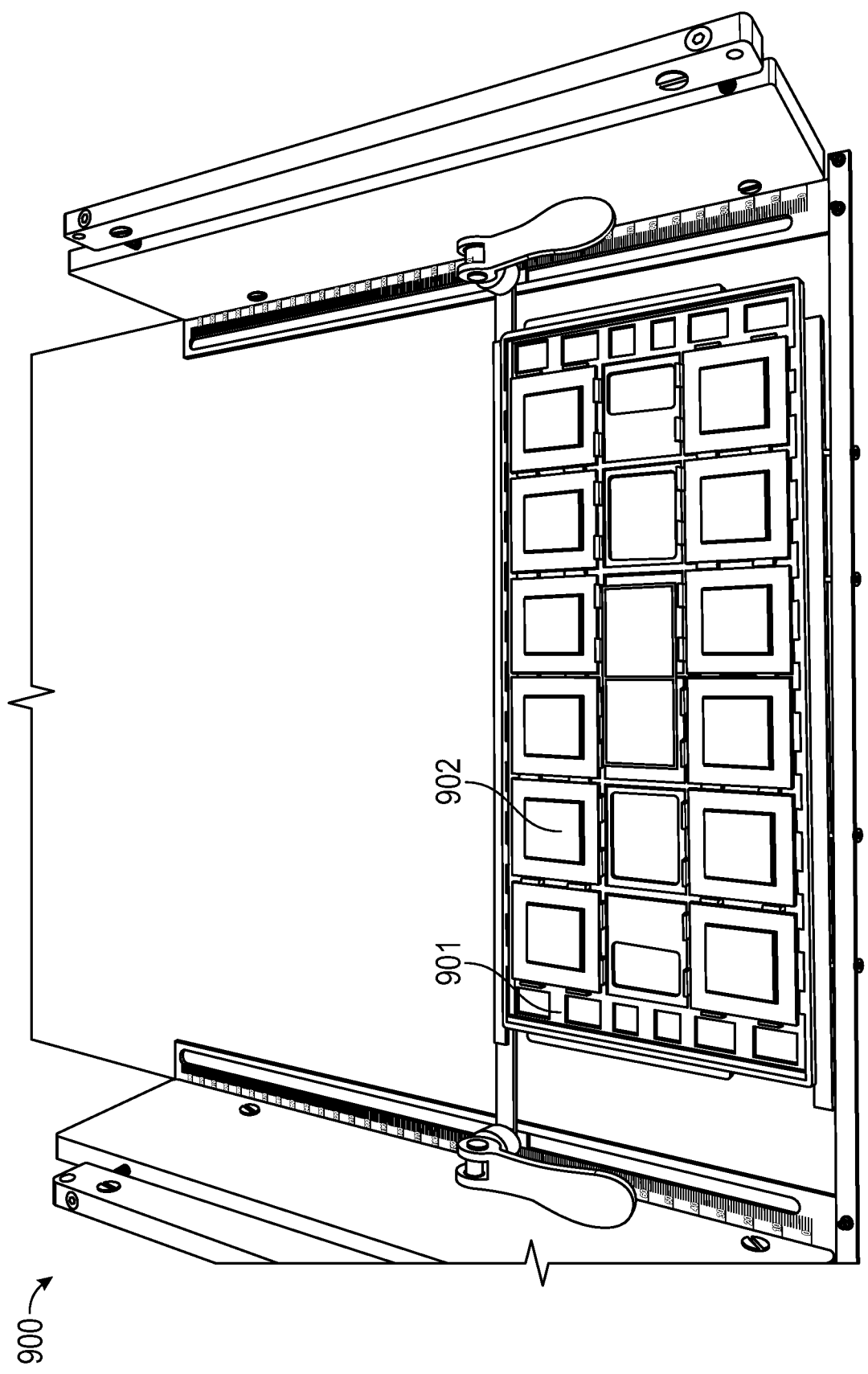
FIG. 9 is a photograph of an adjustable fixture holding a Joint Electron Device Engineering Council (JEDEC) tray, in accordance with a representative embodiment.
Figure 10:
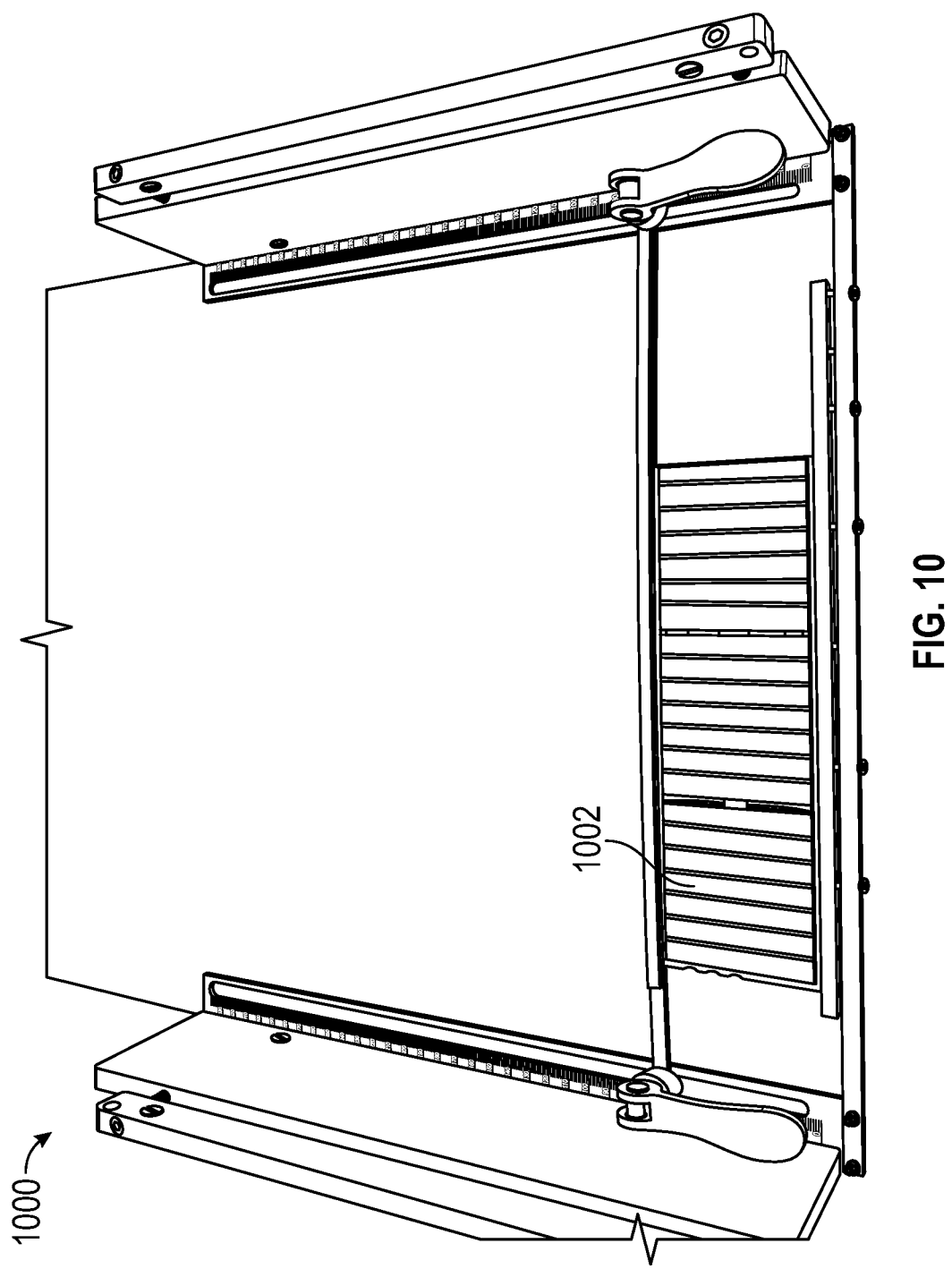
FIG. 10 is a photograph of an adjustable fixture holding a strip sample, in accordance with a representative embodiment.
Figure 11:
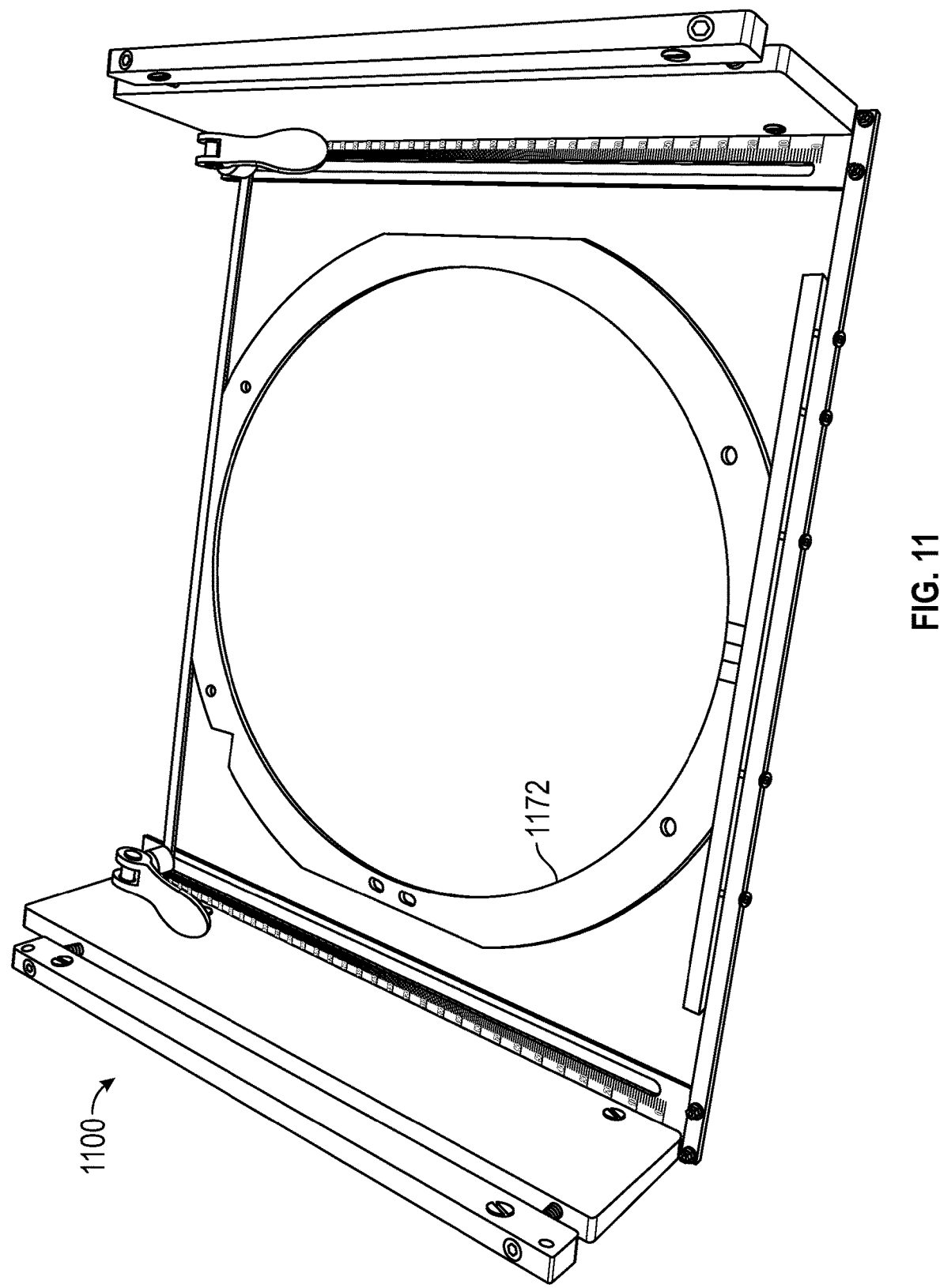
FIG. 11 is a photograph of an adjustable fixture with a wafer holder, in accordance with a representative embodiment.

FIG. 9 is a photograph of an adjustable fixture 900 holding a JEDEC tray 901, in accordance with a representative embodiment. As shown in the figure, the JEDEC tray 901 may be structurally configured to hold one or more samples 902 therein. FIG. 10 is a photograph of an adjustable fixture 1000 holding one or more samples 1002, which may include a strip sample, in accordance with a representative embodiment. FIG. 11 is a photograph of an adjustable fixture 1100 holding a wafer holder 1172, in accordance with a representative embodiment.

Thus, as demonstrated by way of example in FIGS. 9-11, the fixture may be adjustable to support different types of samples, e.g., for inspection in a tank of a scanning acoustic microscope. As discussed above, the fixture may hold a sample (where samples may include a wafer up to 300 mm in size, or larger, or flexible strips, which may be warped or curved), a holder configured to hold or secure a sample, an adapter plate (such as a plastic baffle plate), a JEDEC tray (e.g., with a provision to hold it flat), and so on. The fixture may be configured to hold a sample flat without damaging (e.g., scratching) the sample. In certain implementations, the sample mold compound can be very thin, e.g., less than 1 mm. For proper sample support, it may be desirable that no part of the fixture is disposed significantly above the top of a sample so that the fixture does not interfere with an ultrasonic transducer or the like during scanning and inspection. The present teachings may make it easy for a user to switch between different sample types, while also making it simple for a user to place samples into a fixture without the use of tools.

Figure 12:
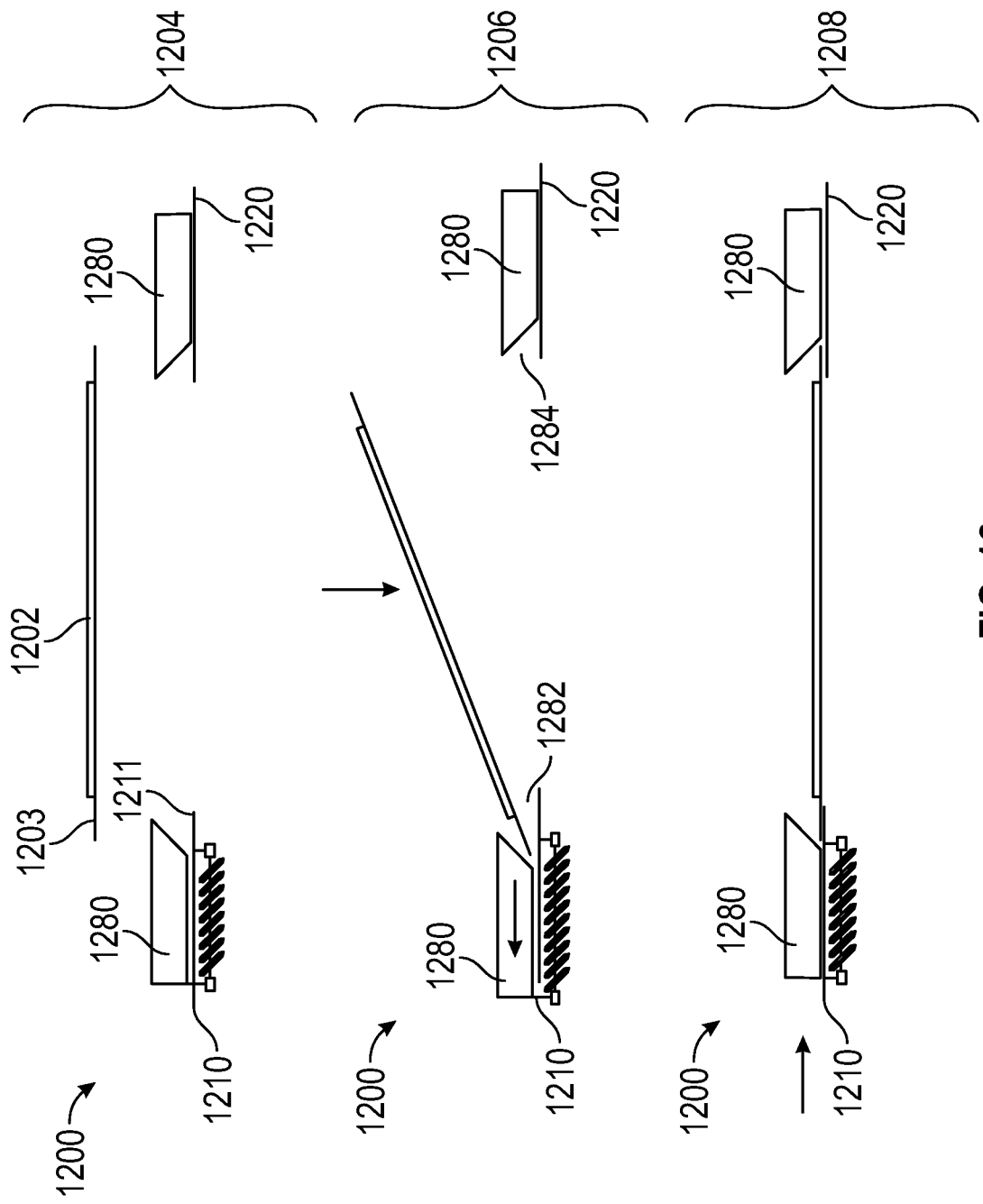
FIG. 12 illustrates insertion of a sample into an adjustable fixture, in accordance with a representative embodiment.

FIG. 12 illustrates insertion of a sample 1202 into an adjustable fixture 1200, in accordance with a representative embodiment. In general, the figure shows three parts of a process for inserting a sample 1202 into an adjustable fixture 1200—a first part 1204, a second part 1206, and a third part 1208.

The figure further shows a first horizontal bar 1210 and a second horizontal bar 1220, which each include one or more clamp jaws 1280. Specifically, one or more of the first horizontal bar 1210 and the second horizontal bar 1220 may include a clamp jaw 1280 structurally configured to hold the sample 1202, or the sample and an adapter plate 1203. The clamp jaw 1280 may thus be disposed on one or more of the horizontal bars, e.g., where it is movable relative to the horizontal bars against a spring force. Movement of the clamp jaw 1280 toward one or more of the first end of the frame or the second end of the frame may create a channel for receiving an end of the sample 1202.

For example, the clamp jaw 1280 may be disposed on the first horizontal bar 1210 and may be movable relative to the first horizontal bar 1210 against a spring force, where movement of the clamp jaw 1280 toward the first end of the frame creates a first channel 1282 for receiving the first end of the sample 1202. The clamp jaw 1280 may also or instead be disposed on the second horizontal bar 1220 and may be movable relative to the second horizontal bar 1220 against a spring force, where movement of the clamp jaw 1280 toward the second end of the frame creates a second channel 1284 for receiving the second end of the sample 1202. In other embodiments, the clamp jaw 1280 is disposed on each of the first horizontal bar 1210 and the second horizontal bar 1220, but the clamp jaw 1280 on one or more of the horizontal bars is fixed, e.g., the clamp jaw 1280 on the second horizontal bar 1220 may be fixed while the clamp jaw 1280 on the first horizontal bar 1210 is movable. Regardless of whether the clamp jaw 1280 on the second horizontal bar 1220 is fixed or movable, the clamp jaw 1280 on the second horizontal bar 1220 may include the second channel 1284 for receiving the second end of the sample 1202.

As shown in FIG. 12, the clamp jaw 1280 may be engaged with a top surface 1211 of one or more of the first horizontal bar 1210 and the second horizontal bar 1220. However, other configurations are also or instead possible. For example, the clamp jaw 1280 may be engaged with an interior surface of one or more of the first horizontal bar 1210 and the second horizontal bar 1220. A clamp jaw 1280 may thus include one or more of the first face and the second face as described herein, e.g., the faces or surfaces that contact (partially or wholly) the edges or ends of the sample 1202.

Further, one or more of the first horizontal bar 1210, the second horizontal bar 1220, and the clamp jaw 1280 may be engaged with another frame member. For example, a fixed frame member or a movable frame member such as the first support member as described herein. The frame member may also or instead include a stepped surface, e.g., as described below with reference to FIG. 15.

Thus, turning back to FIG. 12, two clamp jaws 1280 (one that is spring loaded and movable, and one that is fixed) may be used to hold a sample 1202. As shown in the first part 1204 and the second part 1206, the clamp jaw 1280 that is movable may slide away from the opposite clamp jaw 1280 against a spring force. In the second part 1206, a first end or edge of the sample 1202 may be positioned to engage the first channel 1282, which is created by sliding the clamp jaw 1280 away from the opposite clamp jaw 1280. In the third part 1208, a second end or edge of the sample 1202 may be placed in the second channel 1284, which may be present adjacent to, or disposed in, a fixed clamp jaw 1280, or which may be created by a sliding clamp jaw 1280. One or more of the sliding/movable clamp jaws 1280 may then be released, where the sample 1202 is then held firmly in place by the spring loading of one or more of the clamp jaws 1280.

FIG. 13 illustrates an adjustable fixture 1300 holding a sample 1302, in accordance with a representative embodiment, and FIG. 14 illustrates clamp jaws 1380 of the adjustable fixture 1300, which may be used to hold a sample 1302 or a support surface 1392 therebetween. FIG. 13 further shows a spring element 1316, which may be disposed between one or more of the clamp jaws 1380 and a horizontal bar or other frame member 1386, such that one or more of the clamp jaws 1380 is spring loaded. Stated otherwise, one or more of the clamp jaws 1380 may be spring loaded, using the spring element 1316 that reacts against a support member or frame member 1386, which may be fixed to the frame of the adjustable fixture 1300.

As shown in FIGS. 13 and 14, one or more clamping surfaces 1388 of the clamp jaws 1380 may include a groove 1389, e.g., a tapered groove or "v-groove" that is structurally configured to provide accurate and repeatable positioning of a sample 1302 therein. In this manner, once the horizontal bars of the adjustable fixture 1300 are properly positioned, multiple samples 1302 may be loaded quickly and easily by slotting a sample 1302 into the groove 1389. Slotting the sample 1302 into the grooves 1389 may first occur in a spring-loaded horizontal bar, where an end of the sample 1302 presses a portion of the horizontal bar against a spring element 1316 or the like to allow an opposite end of the sample 1302 to be loaded into a corresponding groove 1389 of a corresponding horizontal bar, where releasing the force against the spring-loaded horizontal bar may press the sample into place. By design, the groove 1389 may help to flatten warpage of the sample 1302. Grooves 1389 or slots with profiles other than those shown in the figures may also or instead be used.

Figure 15:
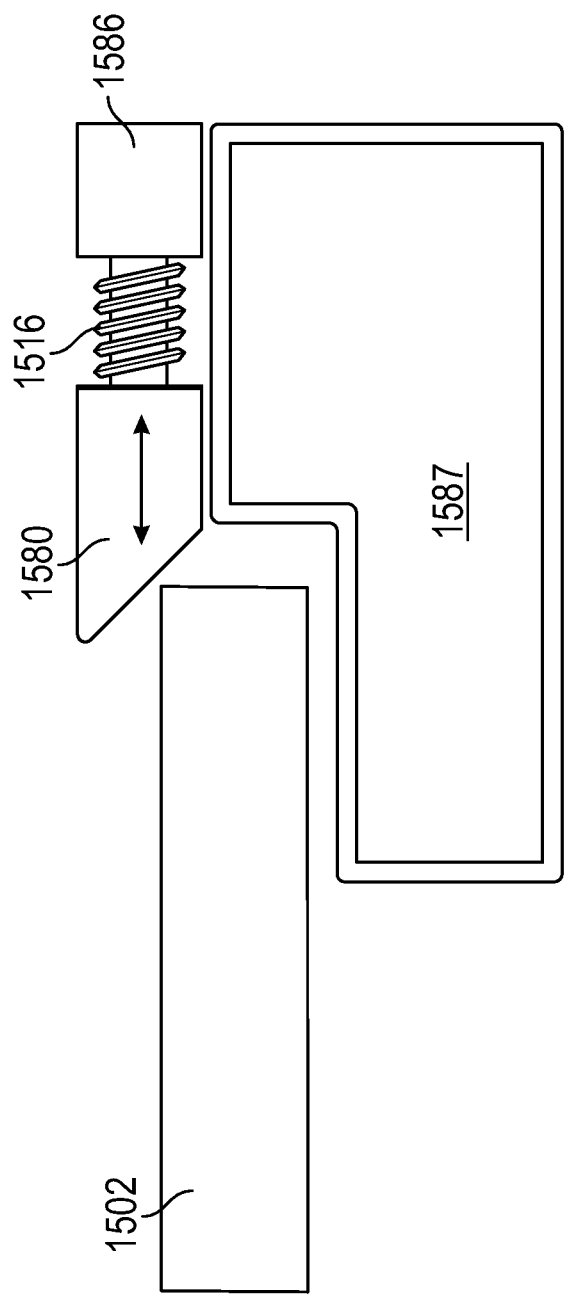
FIG. 15 illustrates a cross-sectional view of an adjustable fixture holding a sample, in accordance with a representative embodiment.

FIG. 15 illustrates a cross-sectional view of an adjustable fixture holding a sample 1502, in accordance with a representative embodiment. Specifically, the sample 1502 is shown as being held in place by a clamp jaw 1580 that is spring loaded relative to a frame member 1586 via a spring element 1516. The sample 1502 may also or instead be supported on a stepped surface 1587 of the frame of the adjustable fixture, e.g., for providing accurate and repeatable positioning of the sample 1502. In certain implementations, one or more of the clamp jaw 1580, the frame member 1586, and the stepped surface 1587 is disposed on a horizontal bar.

FIG. 16 illustrates an adjustable fixture 1600 holding a sample 1602, in accordance with a representative embodiment. As shown in the figure, the adjustable fixture 1600 may include one or more clamps 1690. The clamps 1690 may include hold-down clamps or the like, which are structurally configured to hold down edges of the sample 1602 (or a holder, adapter plate, or similar). The clamps 1690 may be positioned on a support surface 1692. The support surface 1692 may be included on one or more of a horizontal bar, a side bar, a frame member, a support member, an adapter plate, a wafer holder (or other sample holder), and combinations thereof. The positions of the clamps 1690 may be adjustable, e.g., as further shown in FIGS. 17 and 18 described below.

FIG. 17 is a photograph of a clamp 1690 of an adjustable fixture holding a sample 1602, in accordance with a representative embodiment, e.g., an embodiment similar to that described above with reference to FIG. 16. As shown in FIG. 17, the clamp 1690 may be adjustably attached to a support surface 1692 via a screw element 1694 (or other hold-down element as is known in the art). The screw element 1694 may be structurally configured to allow for rotation of the clamp 1690.

Figure 18:
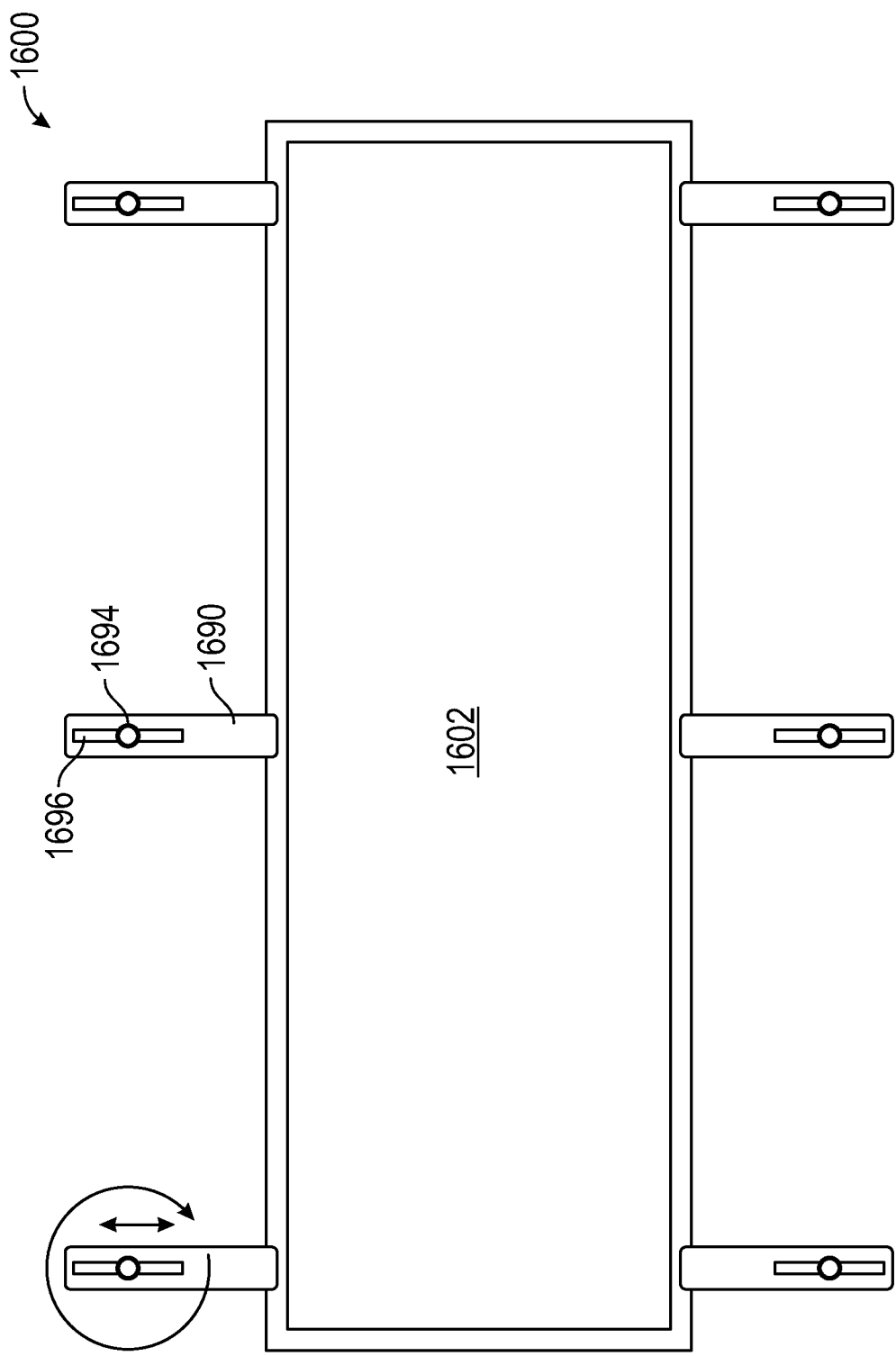
FIG. 18 illustrates an adjustable fixture holding a sample, in accordance with a representative embodiment.

FIG. 18 illustrates an adjustable fixture 1600 holding a sample 1602, in accordance with a representative embodiment, e.g., an embodiment similar to those described above with reference to FIGS. 16-17. As shown in FIG. 18, multiple clamps 1690 may be used to hold the sample 1602, where one or more of the clamps 1690 is adjustable. In such embodiments, the clamps 1690 may be coupled using screw elements 1694 or the like (e.g., thumbscrews) that pass through slotted holes 1696 or the like in the clamps 1690. This configuration may allow the clamps 1690 to be both rotatable and slidable relative to a support surface, e.g., to allow for samples 1602 of different sizes, as well as to allow easy insertion and removal of samples 1602.

Figure 19:
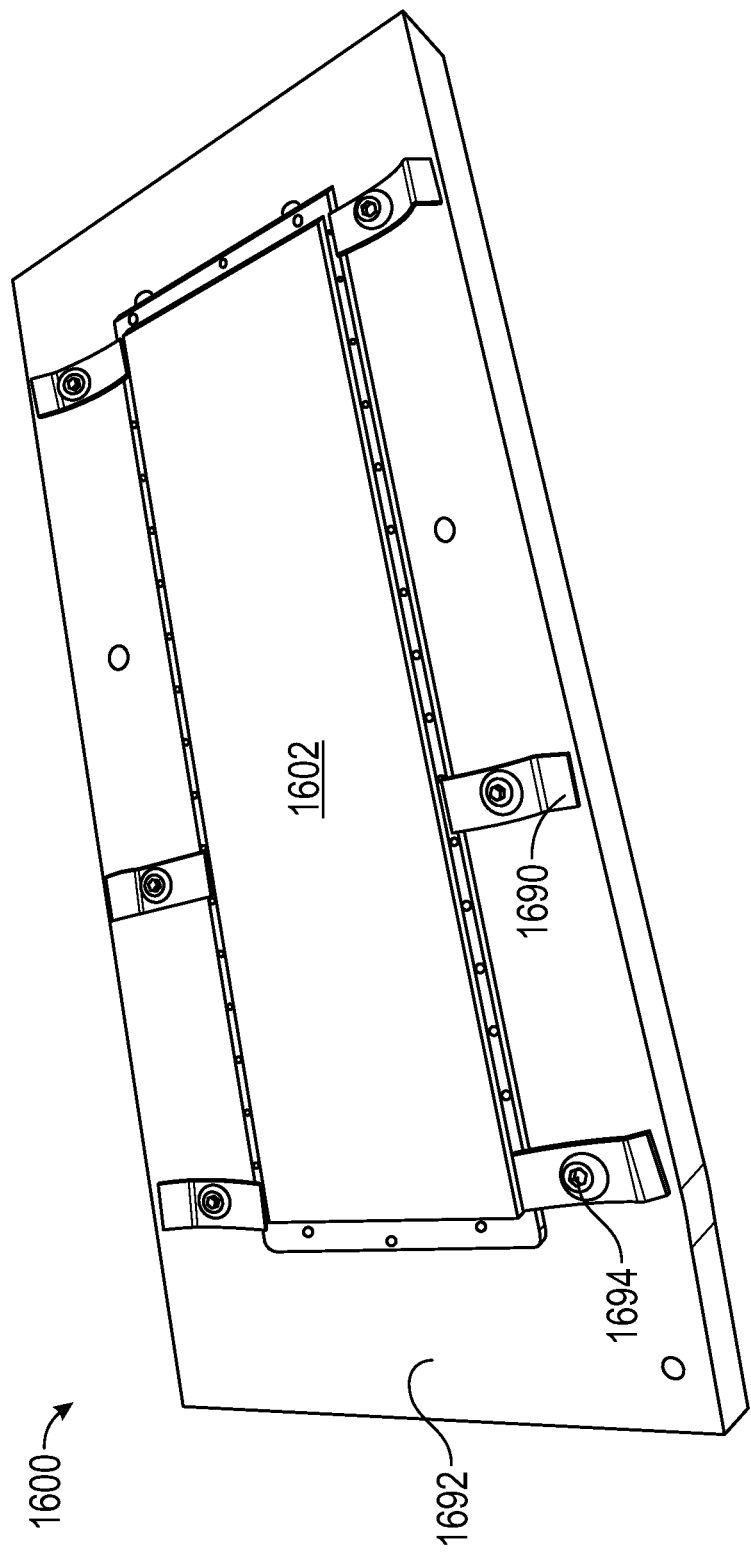
FIG. 19 is a photograph of a portion of an adjustable fixture holding a sample, in accordance with a representative embodiment.

FIG. 19 is a photograph of an adjustable fixture 1600 holding a sample 1602, in accordance with a representative embodiment, e.g., an embodiment similar to those described above with reference to FIGS. 16-18. Thus, as shown in FIGS. 16-19, the adjustable fixture 1600 may include a clamp 1690, where the clamp 1690 is adjustable. For example, the clamp 1690 may be slidably engaged on a component of the frame, e.g., on one or more of the first horizontal bar, the second horizontal bar, the side bar, a support surface 1692, an adapter plate, and a frame member. The clamp 1690 may further be lockable on a component of the frame, e.g., lockable along one or more of the first horizontal bar and the second horizontal bar. Adjustability and lockability may be provided by a screw element 1694 or the like. For example, the clamp 1690 may include a slotted hole, where the screw element 1694 is disposed therethrough for slidable adjustment of the clamp 1690. The clamp 1690 may further be rotatable.

Figure 20:
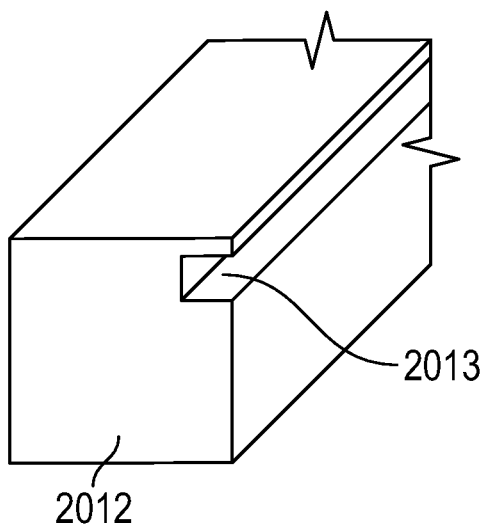
FIG. 20 illustrates a guide rail of an adjustable fixture, in accordance with a representative embodiment.

FIG. 20 illustrates a guide rail 2012 of an adjustable fixture, in accordance with a representative embodiment. The guide rail 2012 may include a slot 2013, where the slot 2013 is structurally configured to receive an edge (or otherwise an end) of a sample. The slot 2013 may also or instead be structurally configured to receive an edge of one or more of a support surface and an adapter plate. The guide rail 2012 may be disposed on one or more of a horizontal bar (e.g., the first horizontal bar and the second horizontal bar as described herein), a side bar, a support member, an adapter plate, or otherwise on a frame member. An adjustable fixture may include a plurality of guide rails 2012, e.g., a first guide rail on a first horizontal bar and a second guide rail on a second horizontal bar, so as to hold opposite edges of a sample.

Figure 21:
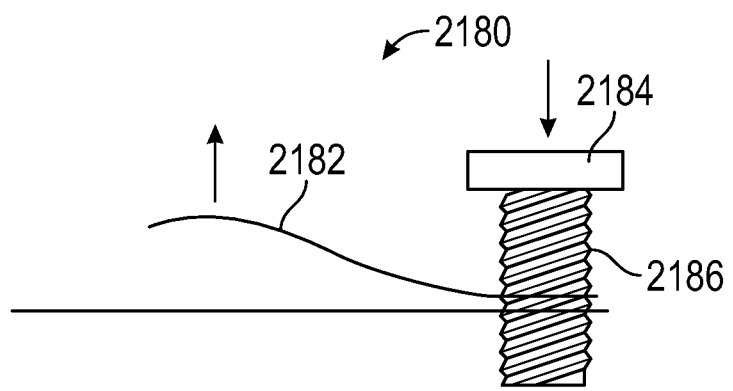
FIG. 21 illustrates a spring clamp of an adjustable fixture, in accordance with a representative embodiment.

FIG. 21 illustrates a clamp 2180 (e.g., a spring clamp) of an adjustable fixture, in accordance with a representative embodiment. The clamp 2180 may include one or more of a hold-down arm 2182, a push-down element 2184, and a spring element 2186. In operation, and as shown in the figure, a downward force on the push-down element 2184 may compress the spring element 2186 causing the hold-down arm 2182 to rise and enable insertion or removal of a sample or an adapter plate. The hold-down arm 2182 may thus be spring loaded, but other types of hold-down arms 2182 may be used. A benefit of this approach may include that no tools may be needed when inserting or removing a sample. The clamp 2180 may be used to supplement or replace any other clamps or hold-down elements as described elsewhere herein. For example, the clamp 2180 may be disposed on one or more of a horizontal bar, a side bar, a support member, an adapter plate, or otherwise on a frame member.

Figure 22:
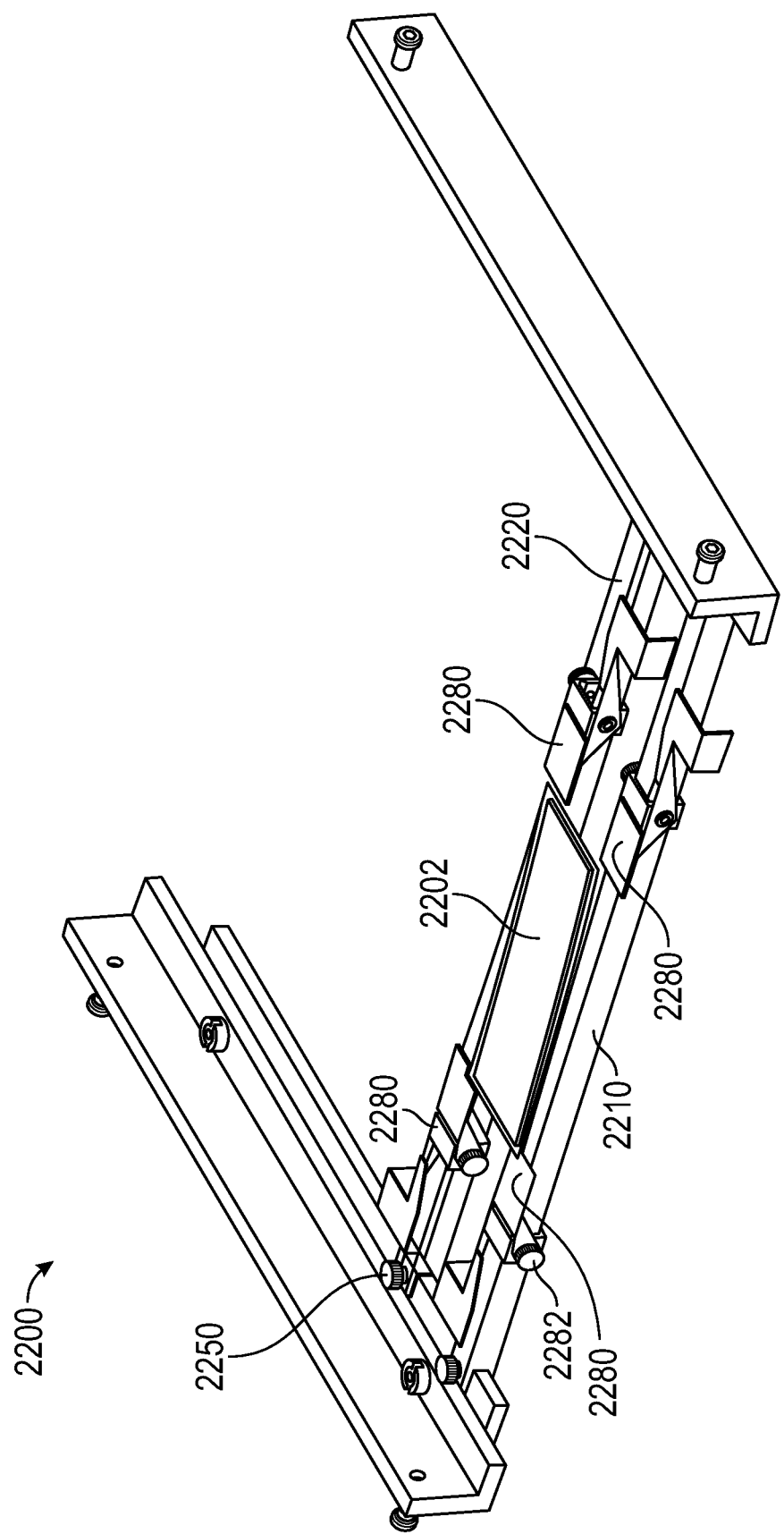
FIG. 22 illustrates an adjustable fixture holding a sample, in accordance with a representative embodiment.

FIG. 22 illustrates an adjustable fixture 2200 holding a sample 2202, in accordance with a representative embodiment. The adjustable fixture 2200 shown in FIG. 22 may include one or more sample locator mechanisms 2280 disposed on one or more of the horizontal bars, e.g., the first horizontal bar 2210 and the second horizontal bar 2220. The sample locator mechanisms 2280 may be structurally configured to secure a position of the sample 2202 relative to the frame of the adjustable fixture 2200. The sample locator mechanisms 2280 may be slidable along one or more of the horizontal bars, and may further include locking mechanisms 2282 to secure or lock a position of the sample locator mechanisms 2280 along the horizontal bar. The locking mechanisms 2282 may include thumbscrews, pins, bolts, screws, or the like. As shown in FIG. 22, the sample locator mechanisms 2280 may be formed as, or may otherwise include, clamps or the like. In operation, the horizontal bars and the sample locator mechanisms 2280 may be adjusted for a desired sample size, where the sample locator mechanisms 2280 may be structurally configured to insert and release a sample 2202.

FIG. 22 also shows engagement mechanisms 2250 in the form of thumbscrews, which may be rotated to secure or lock a position of one or more of the first horizontal bar 2210 and the second horizontal bar 2220, which may each be independently movable.

Figure 23:
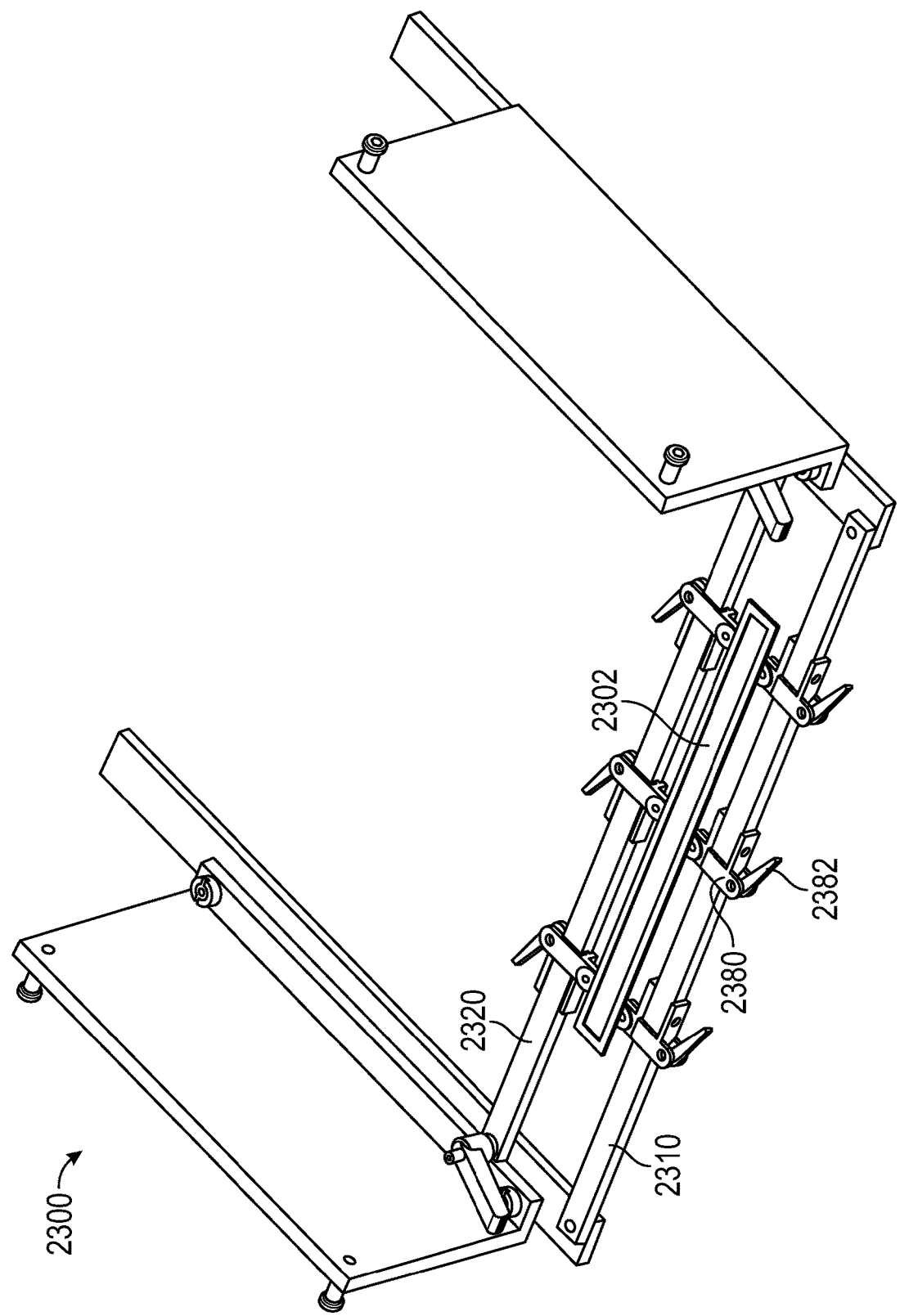
FIG. 23 illustrates an adjustable fixture holding a sample, in accordance with a representative embodiment.

FIG. 23 illustrates an adjustable fixture 2300 holding a sample 2302, in accordance with a representative embodiment. This figure includes an alternate embodiment of the sample locator mechanisms 2380 disposed on one or more of the horizontal bars, e.g., the first horizontal bar 2310 and the second horizontal bar 2320. Specifically, the sample locator mechanisms 2380 may be slidable along the horizontal bars, and may further include locking mechanisms 2382 to secure or lock a position of the sample locator mechanisms 2280 along the horizontal bars, where the locking mechanisms 2382 include spring grips or the like. The locking mechanisms 2382 may also or instead be used to adjust portions of the sample locator mechanisms 2380 that are engaged with the sample 2302, e.g., to lock a sample 2302 in a specific position within the adjustable fixture 2300.

FIG. 24 illustrates spring clamps 2480 of an adjustable fixture, in accordance with a representative embodiment. The spring clamps 2480 may include a hold-down arm 2482 and a spring element 2486. Torsion in the spring element 2486 may be applied to the hold-down arm 2482, which, in turn, holds an edge of a sample 2402.

FIG. 25 illustrates clamps 2580 of an adjustable fixture 2500, in accordance with a representative embodiment. The adjustable fixture 2500 may further include at least one of a guide 2582 and a fin 2584 for controlling positions of at least a portion of the clamp 2580. The guides 2282 and fins 2584 may control the movement of the clamps 2580 to secure the sample 2502. Spring elements 2586 may be used to clamp the sample 2502, where the spring elements 2586 may be disposed on an underside of a support surface as shown in the figure.

Figure 26:
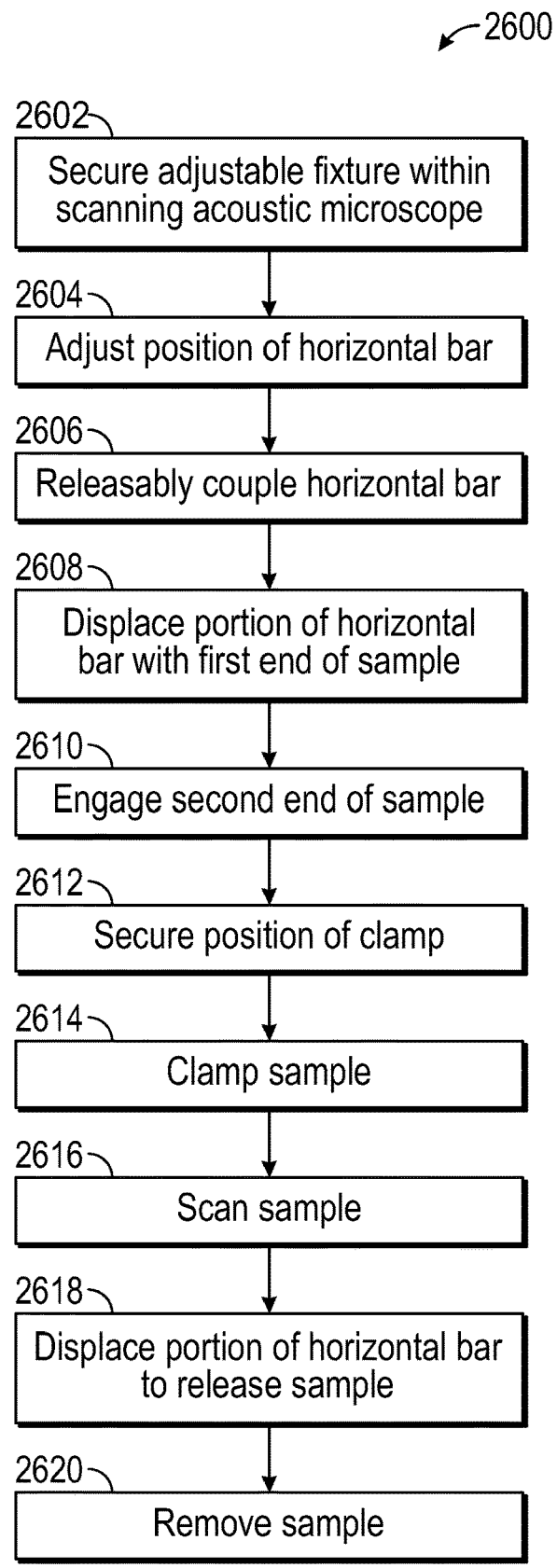
FIG. 26 is a flow chart of a method for inspecting a sample, in accordance with a representative embodiment.

FIG. 26 is a flow chart of a method 2600 for inspecting a sample, in accordance with a representative embodiment. The method 2600 may include the use of one or more of the adjustable fixtures as discussed herein, e.g., for securing a sample for inspection with a scanning acoustic microscope.

As shown in block 2602, the method 2600 may include securing an adjustable fixture within a scanning acoustic microscope. As described above, the adjustable fixture may include a frame, a first horizontal bar that is spring loaded on a first end of the frame, and a second horizontal bar that is movable between the first end and a second end of the frame.

As shown in block 2604, the method 2600 may include adjusting a position of the second horizontal bar between the first end and the second end of the frame. Adjusting the position of the second horizontal bar between the first end and the second end of the frame may include sliding the second horizontal bar along a side bar.

As shown in block 2606, the method 2600 may include releasably coupling the second horizontal bar at a desired position on the side bar using an engagement mechanism.

As shown in block 2608, the method 2600 may include displacing, using a first end of a sample, at least a portion of the first horizontal bar toward the first end of the frame by applying a force greater than a predetermined spring force.

As shown in block 2610, the method 2600 may include engaging a second end of the sample with the second horizontal bar. Engaging the second end of the sample with the second horizontal bar may include placing the second end of the sample within a groove in the second horizontal bar. The predetermined spring force may secure the sample between the first horizontal bar and the second horizontal bar. The engagement of the sample between the horizontal bars may act to flatten the sample, and thus, the method 2600 may further include flattening warpage of the sample.

As shown in block 2612, the method 2600 may include sliding a clamp (or other sample locator mechanism) along at least one of the first horizontal bar and the second horizontal bar toward the sample, and securing a position of the clamp (or other sample locator mechanism) along the horizontal bar.

As shown in block 2614, the method 2600 may include clamping the sample using the clamp (or other sample locator mechanism) to further secure the sample.

As shown in block 2616, the method 2600 may include scanning the sample, e.g., with a scanning acoustic microscope. In certain implementations, the scanning of the sample includes a through transmission inspection of the sample.

As shown in block 2618, the method 2600 may include displacing at least a portion of the first horizontal bar toward the first end of the frame by applying a force greater than the predetermined spring force to release the sample.

As shown in block 2620, the method 2600 may include removing the sample. Removing the sample may include releasing the second end of the sample from engagement with the second horizontal bar when the portion of the first horizontal bar is displaced, and releasing the first end of the sample from engagement with the first horizontal bar.

Thus, in general, the method 2600 may include positioning a moveable horizontal bar according to a depth of a sample to be held in an adjustable fixture, and locking the horizontal bar in place. A first horizontal bar, a second horizontal bar, or both horizontal bars may be moved. A first edge of the sample may be located in a groove in one of the horizontal bars, which may be spring loaded, and pushed to decompress the spring loading. The spring-loaded horizontal bar may be moved by the exerted force (greater than the spring force) enabling a second edge of the sample to be located in a groove in the other horizontal bar. The force on the sample may then be released, where the spring-loaded horizontal bar moves back and the sample is gripped between the two horizontal bars. The grooves in the horizontal bars may ensure that the sample is positioned accurately (and can be repeatedly positioned accurately), and may help to minimize sample warpage. The sample may then be scanned. After scanning, the sample is pushed back into the spring-loaded horizontal bar to compress the spring elements and move the horizontal bar such that the sample can be removed from the groove in the other horizontal bar. The sample may then be removed completely. If another sample is to be scanned, the process may repeat itself. If the next sample to be scanned is not the same size as the previous sample, the moveable horizontal bar may be repositioned to accommodate the next sample.

It will be appreciated that the devices, systems, and methods described above are set forth by way of example and not of limitation. Absent an explicit indication to the contrary, the disclosed steps may be modified, supplemented, omitted, and/or re-ordered without departing from the scope of this disclosure. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context.

The method steps of the implementations described herein are intended to include any suitable method of causing such method steps to be performed, consistent with the patentability of the following claims, unless a different meaning is expressly provided or otherwise clear from the context. So, for example performing the step of X includes any suitable method for causing another party such as a remote user, a remote processing resource (e.g., a server or cloud computer) or a machine to perform the step of X. Similarly, performing steps X, Y, and Z may include any method of directing or controlling any combination of such other individuals or resources to perform steps X, Y, and Z to obtain the benefit of such steps. Thus, method steps of the implementations described herein are intended to include any suitable method of causing one or more other parties or entities to perform the steps, consistent with the patentability of the following claims, unless a different meaning is expressly provided or otherwise clear from the context. Such parties or entities need not be under the direction or control of any other party or entity, and need not be located within a particular jurisdiction.

It should further be appreciated that the methods above are provided by way of example. Absent an explicit indication to the contrary, the disclosed steps may be modified, supplemented, omitted, and/or re-ordered without departing from the scope of this disclosure.

It will be appreciated that the methods and systems described above are set forth by way of example and not of limitation. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context. Thus, while particular embodiments have been shown and described, it will be apparent to those skilled in the art that various changes and modifications in form and details may be made therein without departing from the scope of this disclosure and are intended to form a part of the disclosure as defined by the following claims, which are to be interpreted in the broadest sense allowable by law.

The various representative embodiments, which have been described in detail herein, have been presented by way of example and not by way of limitation. It will be understood by those skilled in the art that various changes may be made in the form and details of the described embodiments resulting in equivalent embodiments that remain within the scope of the appended claims.

What is claimed is:

1. An adjustable fixture for holding a sample for inspection with a scanning acoustic microscope, comprising:
    a frame comprising a first end, a second end, a first side, and a second side; a first horizontal bar disposed on the first end of the frame, the first horizontal bar comprising a first face structurally configured for engagement with a first end of a sample;
    a second horizontal bar disposed on the second end of the frame, the second horizontal bar comprising a second face opposing the first face, the second face structurally configured for engagement with a second end of the sample, the second horizontal bar engaged with the frame to be movable between the first end and the second end of the frame;
    a side bar disposed on one or more of the first side and the second side of the frame, with an end of the second horizontal bar slidable and lockable along the side bar; and
    an engagement mechanism releasably coupling the end of the second horizontal bar to the side bar, a protuberance disposed on one or more of the engagement mechanism and the end of the second horizontal bar and the protuberance sized and shaped for engagement with the side bar;

the adjustable fixture being configured to secure the sample on its edges such that an underside and an upper side of the sample are unobstructed to allow for one or more of through transmission inspection and pulse echo inspection of a plurality of types of samples during inspection with the scanning acoustic microscope.

2. The adjustable fixture of claim 1, where the first horizontal bar is spring loaded via one or more spring elements.

3. The adjustable fixture of claim 2, where the first face is movable toward the first end of the frame when a force greater than a spring force of the one or more spring elements is applied thereto.

4. The adjustable fixture of claim 3, where the spring force is selected to allow the first face to move toward the first end of the frame when receiving the first end of the sample, and to secure the sample on the frame when the second end of the sample is engaged with the second face of the second horizontal bar.

5. The adjustable fixture of claim 2, further comprising a first support member engaged to the first horizontal bar via the one or more spring elements and movable relative to the first horizontal bar via a predetermined spring force applied thereto, the first support member comprising the first face that is structurally configured for engagement with the first end of the sample.

6. The adjustable fixture of claim 1, where the first horizontal bar comprises a first groove on the first face, and where the second horizontal bar comprises a second groove on the second face.

7. The adjustable fixture of claim 6, where one or more of the first groove and the second groove is tapered.

8. The adjustable fixture of claim 7, where tapering of one or more of the first groove and the second groove is structurally configured to flatten warpage of the sample when the sample is secured between the first horizontal bar and the second horizontal bar.

9. The adjustable fixture of claim 1, where the first horizontal bar is fixed on the first end of the frame.

10. The adjustable fixture of claim 1, where the first horizontal bar is movable between the first end and the second end of the frame.

11. The adjustable fixture of claim 1, where one or more of the side bar, the first horizontal bar, and the second horizontal bar comprises one or more markings corresponding to different sample types for configuring the adjustable fixture to hold at least one of the different sample types.

12. The adjustable fixture of claim 1, where the side bar comprises a slot, and the protuberance is sized and shaped for engagement with the slot.

13. The adjustable fixture of claim 12, where the protuberance is structurally configured to prevent rotation of the second horizontal bar relative to the side bar, and to maintain a predetermined alignment of the second horizontal bar with the first horizontal bar.

14. The adjustable fixture of claim 1, where the engagement mechanism comprises a release mechanism.

15. The adjustable fixture of claim 1, further comprising an adapter plate structurally configured for placement and securement between the first horizontal bar and the second horizontal bar, the adapter plate sized and shaped to hold a predetermined sample.

16. The adjustable fixture of claim 1, where one or more of the first horizontal bar and the second horizontal bar comprise a clamp jaw structurally configured to hold the sample.

17. The adjustable fixture of claim 16, where one or more of the first horizontal bar, the second horizontal bar, and the clamp jaw are engaged with a frame member including a stepped surface.

18. The adjustable fixture of claim 1, further comprising a first side wall disposed on the first side of the frame, and a second side wall disposed on the second side of the frame, where each of the first side wall and the second side wall is sized and shaped for alignment with a wall of an immersion tank of the scanning acoustic microscope.

19. The adjustable fixture of claim 18, where the first side wall and the second side wall are structurally configured to maintain a predetermined alignment between a sample plane of the frame and a scanning plane of the scanning acoustic microscope, where the sample plane of the frame intersects both the first horizontal bar and the second horizontal bar.

20. The adjustable fixture of claim 1, further comprising one or more leveling elements structurally configured to align the frame with a scanning plane of the scanning acoustic microscope.

21. The adjustable fixture of claim 1, further comprising a sample locator mechanism disposed on one or more of the first horizontal bar and the second horizontal bar, the sample locator mechanisms structurally configured to secure a position of the sample relative to the frame.

22. The adjustable fixture of claim 1, further comprising a clamp.

23. The adjustable fixture of claim 22, where the clamp is slidably engaged on one or more of the first horizontal bar and the second horizontal bar.

24. A method, comprising:
securing an adjustable fixture within a scanning acoustic microscope, the adjustable fixture comprising a frame, a first horizontal bar that is spring loaded on a first end of the frame, and a second horizontal bar that is movable between the first end and a second end of the frame;
adjusting a position of the second horizontal bar between the first end and the second end of the frame;
securing the position of the second horizontal bar using a protuberance sized and shaped for engagement with a side bar;
displacing, using a first end of a sample, at least a portion of the first horizontal bar toward the first end of the frame by applying a force greater than a predetermined spring force;
engaging a second end of the sample with the second horizontal bar, where the predetermined spring force secures the sample between the first horizontal bar and the second horizontal bar; and
securing the sample on its edges so an underside of the sample and an upper-side of the sample are unobstructed to allow for one or more of through transmission inspection and pulse echo inspection of a plurality of types of samples.

25. The method of claim 24, further comprising scanning the sample with the scanning acoustic microscope.

26. The method of claim 25, where scanning the sample includes the through transmission inspection of the sample.

27. The method of claim 24, where adjusting the position of the second horizontal bar between the first end and the second end of the frame comprises sliding the second horizontal bar along the side bar.

28. The method of claim 27, further comprising releasably coupling the second horizontal bar at a desired position on the side bar using an engagement mechanism.

29. The method of claim 24, further comprising flattening warpage of the sample.

30. An adjustable fixture for holding a sample for inspection with a scanning acoustic microscope, comprising:
a frame comprising a first end, a second end, a first side, and a second side;
a first horizontal bar disposed on the first end of the frame;
a first support member engaged to the first horizontal bar via one or more spring elements and movable relative to the first horizontal bar via a predetermined spring force applied thereto and the first support member having a first face that is structurally configured for engagement with a first end of the sample;
a second horizontal bar disposed on the second end of the frame, the second horizontal bar comprising a second face opposing a first face, the second face structurally configured for engagement with a second end of the sample, the second horizontal bar engaged with the frame to be movable between the first end of the frame and the second end of the frame;
a side bar disposed on one or more of the first side and the second side of the frame, with an end of the second horizontal bar slidable and lockable along the side bar; and
one or more levers as parts of an engagement mechanism releasably coupling the end of the second horizontal bar to the side bar, the fixture being configured to secure the sample on its edges such that an underside of the sample and an upper side of the sample are unobstructed to allow for one or more of through transmission inspection and pulse echo inspection of a plurality of types of samples during inspection with the scanning acoustic microscope.

31. The adjustable fixture of claim 30, where the spring force is selected to allow the first face to move toward the first end of the frame when receiving the first end of the sample, and to secure the sample on the frame when the second end of the sample is engaged with the second face of the second horizontal bar.

32. The adjustable fixture of claim 30, where the first support member comprises a first groove on the first face, and where the second horizontal bar comprises a second groove on the second face.

33. The adjustable fixture of claim 32, where one or more of the first groove and the second groove is tapered and the tapering of one or more of the first groove and the second groove is structurally configured to flatten warpage of the sample when the sample is secured between the first horizontal bar and the second horizontal bar.

34. The adjustable fixture of claim 30, where one or more of the side bar, the first horizontal bar, and the second horizontal bar comprises one or more markings corresponding to different sample types for configuring the adjustable fixture to hold at least one of the different sample types.

35. The adjustable fixture of claim 30, where the one or more levers comprises a release mechanism.

36. The adjustable fixture of claim 30, further comprising an adapter plate structurally configured for placement and securement between the first support member and the second horizontal bar, the adapter plate sized and shaped to hold a predetermined sample.

37. The adjustable fixture of claim 30, further comprising a first side wall disposed on the first side of the frame, and a second side wall disposed on the second side of the frame, where each of the first side wall and the second side wall is sized and shaped for alignment with a wall of an immersion tank of the scanning acoustic microscope.

38. The adjustable fixture of claim 37, where the first side wall and the second side wall are structurally configured to maintain a predetermined alignment between a sample plane of the frame and a scanning plane of the scanning acoustic microscope, where the sample plane of the frame intersects both the first horizontal bar and the second horizontal bar.

39. The adjustable fixture of claim 30, further comprising one or more leveling elements structurally configured to align the frame with a scanning plane of the scanning acoustic microscope.

40. The adjustable fixture of claim 30, further comprising a sample locator mechanism disposed on one or more of the first support member and the second horizontal bar, the sample locator mechanisms structurally configured to secure a position of the sample relative to the frame.

41. The adjustable fixture of claim 30, further comprising a clamp configured to slidably engage one or more of the first horizontal bar and the second horizontal bar.

* * * * *